US008865681B2

(12) United States Patent
Yedgar et al.

(10) Patent No.: US 8,865,681 B2
(45) Date of Patent: Oct. 21, 2014

(54) USE OF LIPID CONJUGATES IN THE TREATMENT OF DISEASES OR DISORDERS OF THE EYE

(75) Inventors: Saul Yedgar, Jerusalem (IL); Yuval Cohen, New York, NY (US)

(73) Assignee: Yissum Research Development Company of the Hebrew Unitersity of Jerusalem, Jerusalem (IL)

( * ) Notice: Subject to any disclaimer, the term of this patent is extended or adjusted under 35 U.S.C. 154(b) by 980 days.

(21) Appl. No.: 11/984,223

(22) Filed: Nov. 14, 2007

(65) Prior Publication Data

US 2008/0113935 A1    May 15, 2008

Related U.S. Application Data

(63) Continuation-in-part of application No. 10/919,523, filed on Aug. 17, 2004, which is a continuation-in-part of application No. 10/790,182, filed on Mar. 2, 2004, now Pat. No. 7,141,552.

(60) Provisional application No. 60/858,706, filed on Nov. 14, 2006, provisional application No. 60/907,785, filed on Apr. 17, 2007.

(51) Int. Cl.
| *A61K 31/715* | (2006.01) |
| *A61K 31/727* | (2006.01) |
| *A61K 31/717* | (2006.01) |
| *A61K 31/726* | (2006.01) |
| *A61K 31/718* | (2006.01) |
| *A61K 47/48* | (2006.01) |
| *A61K 9/00* | (2006.01) |
| *A61K 31/685* | (2006.01) |

(52) U.S. Cl.
CPC ............. *A61K 31/685* (2013.01); *A61K 31/718* (2013.01); *A61K 47/48053* (2013.01); *A61K 31/726* (2013.01); *A61K 31/717* (2013.01); *A61K 31/715* (2013.01); *A61K 31/727* (2013.01); *A61K 9/0048* (2013.01); *A61K 47/4823* (2013.01)
USPC .................. 514/56; 514/54; 514/23; 514/57; 514/42; 514/60; 514/62; 514/78; 536/21; 536/18.7; 536/22.1; 536/123.1

(58) Field of Classification Search
CPC ........... A61K 47/48053; A61K 31/726; A61K 9/0048; A61K 31/727; A61K 31/717; A61K 31/685; A61K 31/715; A61K 31/718; A61K 47/4823
USPC .................. 514/56, 54, 23, 57, 42, 60, 62, 78; 536/21, 18.7, 22.1, 123.1
See application file for complete search history.

(56) References Cited

U.S. PATENT DOCUMENTS

| 2,976,576 A | 3/1961 | Wichterle et al. |
| 3,200,960 A | 8/1965 | Wichterle et al. |
| 3,431,046 A | 3/1969 | Conrad et al. |
| 3,532,679 A | 10/1970 | Steckler |
| 3,542,461 A | 11/1970 | Girard et al. |
| 3,621,079 A | 11/1971 | Leeds et al. |
| 3,639,524 A | 2/1972 | Seiderman |
| 3,700,761 A | 10/1972 | O'Driscoll et al. |
| 3,721,657 A | 3/1973 | Seiderman |
| 3,758,448 A | 9/1973 | Stamberger |
| 3,772,235 A | 11/1973 | Stamberger |
| 3,786,034 A | 1/1974 | Blair et al. |
| 3,803,093 A | 4/1974 | Neefe et al. |
| 3,816,571 A | 6/1974 | O'Driscoll et al. |
| 3,875,211 A | 4/1975 | Steckler |
| 3,937,680 A | 2/1976 | de Carle |
| 3,940,207 A | 2/1976 | Barkdoll |
| 3,948,871 A | 4/1976 | Butterfield et al. |
| 3,949,021 A | 4/1976 | Kunitomo et al. |
| 3,983,083 A | 9/1976 | Kaetsu et al. |
| 3,988,274 A | 10/1976 | Masuhara et al. |
| 4,018,853 A | 4/1977 | Le Boeuf et al. |

(Continued)

FOREIGN PATENT DOCUMENTS

| CA | 2397016 | 7/2001 |
| EP | 0236951 | 9/1987 |
| EP | 0529659 | 3/1993 |
| EP | 0581281 | 2/1994 |
| EP | 0581282 | 2/1994 |

(Continued)

OTHER PUBLICATIONS

International Search Report of Application No. PCT/IL07/01407 mailed on Aug. 21, 2008.

(Continued)

*Primary Examiner* — Shaojia Anna Jiang
*Assistant Examiner* — Michael C Henry
(74) *Attorney, Agent, or Firm* — Mark S. Cohen; Pearl Cohen Zedek Latzer Baratz LLP

(57) ABSTRACT

In one embodiment, the invention provides a method of treating, reducing the incidence, reducing the severity or pathogenesis of an eye disease or disorder in a subject, including, inter alia, retinal detachment, macular degeneration, glaucoma or retinopathy, comprising the step of administering an effective amount of a lipid or phospholipid moiety bound optionally via a spacer to a physiologically acceptable monomer, dimer, oligomer, or polymer via an ester or amide bond, and/or a pharmaceutically acceptable salt or a pharmaceutical product thereof. This invention also provides a contact lens solution comprising a lipid or phospholipid moiety bound optionally via a spacer to a physiologically acceptable monomer, dimer, oligomer, or polymer via an ester or amide bond, and/or a pharmaceutically acceptable salt or a pharmaceutical product thereof.

27 Claims, No Drawings

(56) References Cited

U.S. PATENT DOCUMENTS

| | | | |
|---|---|---|---|
| 4,055,378 | A | 10/1977 | Feneberg et al. |
| 4,062,624 | A | 12/1977 | Hammer |
| 4,064,086 | A | 12/1977 | Cowsar et al. |
| 4,099,859 | A | 7/1978 | Merrill |
| 4,604,376 | A | 8/1986 | Teng |
| 4,624,919 | A | 11/1986 | Kokusho |
| 4,654,327 | A | 3/1987 | Teng |
| 5,034,166 | A | 7/1991 | Rawlings et al. |
| 5,039,459 | A | 8/1991 | Kindt-Larsen |
| 5,064,817 | A | 11/1991 | Yedgar et al. |
| 5,169,636 | A | 12/1992 | Nanba et al. |
| 5,354,853 | A | 10/1994 | Staveski |
| 5,401,511 | A | 3/1995 | Margalit |
| 5,401,777 | A | 3/1995 | Ammon et al. |
| 5,464,942 | A | 11/1995 | Sakurai et al. |
| 5,470,578 | A | 11/1995 | Aoki et al. |
| 5,512,671 | A | 4/1996 | Piantadose |
| 5,587,363 | A | 12/1996 | Henderson |
| 5,707,821 | A | 1/1998 | Rydel et al. |
| 5,719,656 | A | 2/1998 | Bowling |
| 5,733,892 | A | 3/1998 | Sakurai |
| 5,785,975 | A | 7/1998 | Parikh |
| 6,022,866 | A | 2/2000 | Falk et al. |
| 6,043,231 | A | 3/2000 | Pruzanski et al. |
| 6,071,532 | A | 6/2000 | Chaikof et al. |
| 6,162,787 | A | 12/2000 | Sorgente et al. |
| 6,171,614 | B1 | 1/2001 | Chaikof et al. |
| 6,180,596 | B1 | 1/2001 | Tsao |
| 6,325,385 | B1 | 12/2001 | Iwashita |
| 6,654,460 | B1 | 11/2003 | Rodgers |
| 6,656,460 | B2 | 12/2003 | Benita et al. |
| 6,749,813 | B1 | 6/2004 | David |
| 7,034,006 | B2 | 4/2006 | Yedgar et al. |
| 7,141,552 | B2 | 11/2006 | Yedgar et al. |
| 7,393,938 | B2 | 7/2008 | Yedgar |
| 7,504,384 | B2 | 3/2009 | Yedgar et al. |
| 7,608,598 | B2 | 10/2009 | Yedgar |
| 2002/0049183 | A1 | 4/2002 | Yedgar et al. |
| 2003/0144247 | A1* | 7/2003 | Kuwano et al. ................ 514/78 |
| 2003/0219909 | A1* | 11/2003 | Lally et al. .................... 436/518 |
| 2004/0087492 | A1 | 5/2004 | Yedgar |
| 2004/0229842 | A1 | 11/2004 | Yedgar et al. |
| 2005/0079211 | A1 | 4/2005 | Yedgar |
| 2005/0203054 | A1 | 9/2005 | Yedgar |
| 2005/0245464 | A1* | 11/2005 | Yedgar ............................ 514/25 |
| 2006/0189571 | A1 | 8/2006 | Yedgar |

FOREIGN PATENT DOCUMENTS

| | | |
|---|---|---|
| EP | 0581282 B | 2/1994 |
| EP | 1046394 A | 10/2000 |
| EP | 1247532 A1 | 10/2002 |
| JP | 04082893 | 3/1992 |
| JP | 04082893 | 5/1992 |
| JP | 09030970 | 2/1997 |
| JP | 09030979 | 2/1997 |
| JP | 2002345455 | 12/2002 |
| JP | 2003160498 | 3/2003 |
| JP | 2003335801 | 11/2003 |
| JP | 2004018841 | 1/2004 |
| JP | 2004170194 | 6/2004 |
| WO | WO 87/02777 | 5/1987 |
| WO | WO 91/00289 | 1/1991 |
| WO | WO 96/04001 | 2/1996 |
| WO | WO 96/11670 | 4/1996 |
| WO | WO 9628544 | 9/1996 |
| WO | WO 9701330 | 1/1997 |
| WO | WO 97/48337 | 12/1997 |
| WO | WO 9816198 | 4/1998 |
| WO | WO 98/51285 | 11/1998 |
| WO | WO 01/51003 | 7/2001 |
| WO | WO 01/91805 | 12/2001 |
| WO | WO 2005/084307 | 9/2005 |
| WO | WO 2006/084275 A2 | 8/2006 |
| WO | WO 2007/076274 | 7/2007 |
| WO | WO 2008/063520 | 5/2008 |
| WO | WO 2009/013563 | 1/2009 |

OTHER PUBLICATIONS

International Search Report of Application No. PCT/IL07/23913 mailed on Apr. 3, 2008.
Written Opinion of corresponding International application No. PCT/IL2007/001408 dated Mar. 12, 2009.
Extended European search report of EP application No. 07827380 dated Dec. 6, 2011.
Extended European search report of EP application No. 07827381 dated Dec. 9, 2011.
International Search Report for International Application No. PCT/IB2007/004668 mailed on Nov. 23, 2012.
International Preliminary Report on Patentability for International Application No. PCT/IB2007/004668 mailed on Dec. 20, 2012.
Mexican Office Action for Mexican Patent Application No. MX/a2008/001639 dated May 2, 2013.
Ehehalt, R. et al., "Lipid Based Therapy for Ulcerative Colitis—Modulation of Intestinal Mucus Membrane Phospholipids as a Tool to Influence Inflammation," Int. J. Mol. Sci. 2010, 11, 4149-4164.
Extended European Search Report of European Application No. 05808267.8 issued Mar. 15, 2012.
Phyllis, Dan et al., "Inhibition of Type I and Type II Phospholipase A2 by Phosphatidyl-Ethanolamine Linked to Polymeric Carriers," Biochemistry, 1998, 37 (17), pp. 6199-6204.
Cummings, B.S., "Phospholipase $A_2$ as targets for anti-cancer drugs," Biochemical Pharmacology 74 (2007), pp. 949-959.
Kokotos, G. et al., "Novel 2-Oxoamide Inhibitors of Human Group IVA Phospholipase $A_2$," J. Med. Chem., 2002, 45, pp. 2891-2893.
Teitelbaum D, Arnon R, Sela M, Rabinsohn Y, Shapiro D., "Sphingomyelin specific antibodies elicited by synthetic conjugates," Immunochemistry. Nov. 1973; 10(11):735-43.
Weltzien HU, Matthiessen HP, Meyer-Delius M, Zimmermann F, Rüde E, "Acidic "peptidophospholipids", a new class of hapten-bearing cell surface modifying reagents," Mol Immunol. Sep. 1984;21(9):801-10.
Winger TM, Ludovice PJ, Chaikof EL, "Lipopeptide conjugates: biomolecular building blocks for receptor activating membrane-mimetic structures," Biomaterials. Feb. 1996;17(4):437-41.
Office Action of U.S. Appl. No. 11/220,965 dated Mar. 27, 2008.
Office Action of U.S. Appl. No. 11/598,812 dated Dec. 19, 2008.
Office Action of U.S. Appl. No. 10/989,606 dated Sep. 1, 2009.
Supplementary Search Report of European Application No. 05724186.1 dated Nov. 17, 2009.
Ofice Action of Japanese Application No. 2001-551427 dated Nov. 20, 2009.
Albini, A, Iwamoto, Y, Kleinman, HK, Martin, GR, Aaronson, SA, Kozlowski, JM and McEwan, RN (1987) "A rapid in vitro assay for quantitating the invasive potential of tumor cells" Cancer Res 47(12):3239-45.
Balsinde, J, Balboa, MA, Yedgar, S and Dennis, EA (2000) "Group V phospholipase A(2)-mediated oleic acid mobilization in lipopolysaccharide-stimulated P388D(1) macrophages" J Biol Chem 275(7):4783-6.
Beck, G, Yard, BA, Schulte, J, Oberacker, R, Van Ackern, K, Van Der Woude, FJ, Krimsky, M, Kaszkin, M and Yedgar, S (2002) "Inhibition of LPS-induced chemokine production in human lung endothelial cells by lipid conjugates anchored to the membrane" Br J Pharmacol 135(7):1665-74.
Brenner, T, Arnon, R, Sela, M, Abramsky, O, Meiner, Z, Riven-Kreitman, R, Tarcik, N and Teitelbaum, D (2001) "Humoral and cellular immune responses to Copolymer 1 in multiple sclerosis patients treated with Copaxone" J Neuroimmunol 115(1-2):152-60.
Brenner, T, Lisak, RP, Rostami, A, Pleasure, DE and Silberberg, DH (1986) "Astrocytes, oligodendrocytes, and Schwann cells share a common antigenic determinant that cross-reacts with myelin basic protein: identification with monoclonal antibody" J Neurosci 6(7):1925-33.

(56) References Cited

OTHER PUBLICATIONS

Brenner, T, Poradosu, E, Soffer, D, Sicsic, C, Gazit, A and Levitzki, A (1998) "Suppression of experimental autoimmune encephalomyelitis by tyrphostin AG-556" *Exp Neurol* 154(2):489-98.

Cabanas, C and Hogg, N (1993) "Ligand intercellular adhesion molecule 1 has a necessary role in activation of integrin lymphocyte function-associated molecule 1" *Proc Natl Acad Sci U S A* 90(12):5838-42.

Chen, WM, Soria, J, Soria, C, Krimsky, M and Yedgar, S (2002) "Control of capillary formation by membrane-anchored extracellular inhibitor of phospholipase A(2)" *FEBS Lett* 522(1-3):113-8.

Dan, P, Dagan, A, Krimsky, M, Pruzanski, W, Vadas, P and Yedgar, S (1998) "Inhibition of type I and type II phospholipase A2 by phosphatidyl-ethanolamine linked to polymeric carriers" *Biochemistry* 37(17):6199-204.

Darville, T, Yedgar, S, Krimsky, M, Andrews, CW, Jr., Jungas, T and Ojcius, DM (2004) "Protection against *Chlamydia trachomatis* infection in vitro and modulation of inflammatory response in vivo by membrane-bound glycosaminoglycans" *Microbes Infect* 6(4):369-76.

Davidson, FF, Dennis, EA, Powell, M and Glenney, Jr, Jr. (1987) "Inhibition of phospholipase A2 by "lipocortins" and calpactins. An effect of binding to substrate phospholipids" *J Biol Chem* 262(4):1698-705.

Greaves MW and Camp RD (1988) "Prostaglandins, leukotrienes, phospholipase, platelet activating factor, and cytokines: an integrated approach to inflammation of human skin." *Arch Dermatol Res* 280:S33-41.

Krimsky, M, Dagan, A, Aptekar, L, Ligumsky, M and Yedgar, S (2000) "Assessment of intestinal permeability in rats by permeation of inulin-fluorescein" *J Basic Clin Physiol Pharmacol* 11(2):143-53.

Krimsky, M, Yedgar, S, Aptekar, L, Schwob, O, Goshen, G, Gruzman, A, Sasson, S and Ligumsky, M (2003) "Amelioration of TNBS-induced colon inflammation in rats by phospholipase A2 inhibitor" *Am J Physiol Gastrointest Liver Physiol* 285(3):G586-92.

Margolis-Nunno, H, Ben-Hur, E, Gottlieb, P, Robinson, R, Oetjen, J and Horowitz, B (1996) "Inactivation by phthalocyanine photosensitization of multiple forms of human immunodeficiency virus in red cell concentrates" *Transfusion* 36(8):743-50.

Murthy, SN, Cooper, HS, Shim, H, Shah, RS, Ibrahim, SA and Sedergran, DJ (1993) "Treatment of dextran sulfate sodium-induced murine colitis by intracolonic cyclosporin" *Dig Dis Sci* 38(9):1722-34.

Okayasu, I, Hatakeyama, S, Yamada, M, Ohkusa, T, Inagaki, Y and Nakaya, R (1990) "A novel method in the induction of reliable experimental acute and chronic ulcerative colitis in mice" *Gastroenterology* 98(3):694-702.

Schmiel, DH and Miller, VL (1999) "Bacterial phospholipases and pathogenesis" *Microbes Infect* 1(13):1103-12.

Schnitzer, E, Dagan, A, Krimsky, M, Lichtenberg, D, Pinchuk, I, Shinar, H and Yedgar, S (2000) "Interaction of hyaluronic acid-linked phosphatidylethanolamine (HyPE) with LDL and its effect on the susceptibility of LDL lipids to oxidation" *Chem Phys Lipids* 104(2):149-60.

Schnitzer, E, Yedgar, S, Danino, D. Talmon, Y and Lichtenberg, D (1999) "The Interaction of hyaluronic-phosphatidylethanolamine with low density lipoprotein (LDL) and its effect on copper induced LDL oxidation" *Biophysical Journal* 76(1): Part 2.

Schnitzer, E, Pinchuk, I, Fainaru, M, Lichtenberg, D and Yedgar, S (1998) "LDL-associated phospholipase a does not protect LDL against lipid peroxidation in vitro" *Free Radic Biol Med* 24(7-8):1294-303.

Yard, BA, Yedgar, S, Scheele, M, Van Der Woude, D, Beck, G, Heidrich, B, Krimsky, M, Van Der Woude, FJ and Post, S (2002) "Modulation of IFN-gamma-induced immunogenicity by phosphatidylethanolamine-linked hyaluronic acid" *Transplantation* 73(6):984-92.

Yedgar, S, Lichtenberg, D and Schnitzer, E (2000) "Inhibition of phospholipase A(2) as a therapeutic target" *Biochim Biophys Acta* 1488(1-2):182-7.

Soeda et al (Biochemistry 29:5188-5144) Tissue Plasminogen Activator Catalyzed Lys-Plasminogen Activation on Heparin-Inserted Phospholipid Liposomes.

Parish et al (Int. J. Cancer 40: 511-518, "Evidence that sulphated polysaccharides inhibit tumour metastasis by blocking tumour-cell-derived heparanases."

Wang D.P, Matthias Schuster, Yi Fong Wang, Chi Huey Wong "Synthesis of phospholipid-inhibitor conjugates by enzymic transphosphatidylation with phospholipase", J. Am. Chem. Soc.; 1993; 115(23); 10487-10491.

Carey et al, "Contrasting effects of cycloxygenase-1 (cox-1) and cox-2 deficiency in the host response to influenze, a viral infection". Journ. of Immunology 2005, vol. 15: 175 (10): 6878-84.

Albini, A, Iwamoto. Y, Kleinman, HK, Martin. GR, Aaronson, SA, Kozlowski, JM and McEwan, RN (1987) "A rapid in vitro assay for quantitating the invasive potential of tumor cells" *Cancer Res* 47(12):3239-45.

Balsinde, J, Balboa. MA. Yedgar, S and Dennis, EA(2000) "Group V phospholipase A(2)-mediated oleic acid mobilization in lipopolysaccharide-stimulated P388D(1) macrophages" *J Biol Chem* 275(7):4783-6.

Beck, G, Yard, BA, Schulte, J. Oberacker, R, Van Ackern, K, Van Der Woude. FJ. Krimsky, M, Kaszkin. M and Yedgar, S (2002) "Inhibition of LPS-induced chemokine production in human lung endothelial cells by lipid conjugates anchored to the membrane" *Br J Pharmacol* 135(7):1665-74.

Brenner. T. Arnon, R, Sela, M, Abramsky. O. Meiner. Z. Riven-Kreitman, R, Tarcik, N and Teitelbaum, D (2001) "Humoral and cellular immune responses to Copolymer 1 in multiple sclerosis patients treated with Copaxone" *J Neuroimmunol* 115(1-2):152-60.

Brenner. T, Lisak, RP. Rostami. A, Pleasure, DE and Silberberg, DH (1986) "Astrocytes, oligodendrocytes, and Schwann cells share a common antigenic determinant that cross-reacts with myelin basic protein: identification with monoclonal antibody" *J Neurosci* 6(7):1925-33.

Brenner, T, Poradosu, E, Soffer, D, Sicsic. C. Gazit. A and Levitzki. A (1998) "Suppression of experimental autoimmune encephalomyelitis by tyrphostin AG-556" *Exp Neurol* 154(2):489-98.

Cabanas. C and Hogg. N (1993) "Ligand intercellular adhesion molecule 1 has a necessary role in activation of integrin lymphocyte function-associated molecule 1" *Proc Natl Acad Sci U S A* 90(12):5836-42.

Chen, WM, Soria. J. Soria. C. Krimsky. M and Yedgar. S (2002) "Control of capillary formation by membrane-anchored extra cellular inhibitor of phospholipase A(2)" *FEBS Lett* 522(1-3):113-8.

Dan, P, Dagan, A, Krimsky, M, Pruzanski. W. Vadas. P. and Yedgar, S (1998) "Inhibition of type I and type II phospholipase A2 by phosphatidyl-ethanolamine linked to polymeric carriers" *Biochemistry* 37(17):6199-204.

Darville, T, Yedgar, S, Krimsky, M, Andrews, CW. Jr . Jungas. T and Ojcius, DM (2004) "Protection against *Chlamydia trachomatis* infection in vitro and modulation of inflammatory response in vivo by membrane-bound glycosaminoglycans" *Microbes Infect* 6(4):369-76.

Davidson, FF, Dennis, EA, Powell, M and Glenney. Jr, Jr. (1987) "Inhibition of phospholipase A2 by "lipocortins" and calpactins An effect of binding to substrate phospholipids" *J Biol Chem* 262(4):1698-705.

Krimsky, M, Dagan, A, Aptekar. L, Ligumsky, M and Yedgar, S (2000) "Assessment of intestinal permeability in rats by permeation of inulin-fluorescein" *J Basic Clin Physiol Pharmacol* 11(2):143-53.

Krimsky, M, Yedgar, S, Aptekar, L, Schwob, O, Goshen, G, Gruzman, A, Sasson, S and Ligumsky. M (2003) "Amelioration of TNBS-induced colon Inflammation in rats by phospholipase A2 inhibitor" *Am J Physiol Gastrointest Liver Physiol* 285(3):G586-92.

Margolis-Nunno, H, Ben-Nur, E, Gottlieb, P, Robinson, R, Oetjen, J and Horowitz, B (1996) "Inactivation by phthalocyanine photosensitization of multiple forms of human immunodeficiency virus in red cell concentrates" *Transfusion* 36(8):743-50.

(56) References Cited

OTHER PUBLICATIONS

Murthy, SN, Cooper, HS, Shim. H. Shah. RS, Ibrahim, SA and Sedergran, DJ (1993) "Treatment of dextran sulfate sodium-induced murine colitis by intracolonic cyclosporin" *Dig Dis Sci* 38(9):1722-34.

Okayasu. I. Hatakeyama, S, Yamada, M, Ohkusa, T, Inagaki, Y and Nakaya, R (1990) "A novel method in the induction of reliable experimental acute and chronic ulcerative colitis in mice" *Gastroenterology* 98(3):694-702.

Schnitzer. E. Dagan. A. Krimsky, M. Lichtenberg. D, Pinchuk, I; Shinar, H and Yedgar, S (2000) "Interaction of hyaluronic acid-linked phosphatidylethanolamine (HyPE) with LDL and its effect on the susceptibility of LDL lipids to oxidation" *Chem Phys Lipids* 104(2)149-60.

Schnitzer. E, Pinchuk, I, Fainaru, M, Lichtenberg, D and Yedgar, S (1998) "LDL-associated phospholipase A does not protect LDL against lipid peroxidation in vitro" *Free Radic Biol Med* 24(7-8):1294-303.

Yard. BA. Yedgar. S. Scheele, M, Van Der Woude, D, Beck, G, Heidrich, B, Krimsky, M, Van Der Woude, F.J and Post, S (2002) "Modulation of IFN-gamma-induced immunogenicity by phosphatidylethanolamine-linked hyaluronic acid" *Transplantation* 73(6):984-92.

Yedgar, S, Lichtenberg. D and Schnitzer, E (2000) "Inhibition of phospholipase A(2) as a therapeutic target" *Biochim Blophys Acta* 1488(1-2)182-7.

Schnitzer, E., et al (1999) "The Interaction of hyaluronic-phosphatidylethanolamine with low density lipoprotein (LDL) and it's effect on copper induced LDL oxidation" (Biophysical Journal vol. 76. No 1 Part 2.

Prostaglandins, leukotrienes, phospholipase, platelet activating factor. and cytokines: an integrated approach to inflammation of human skin Greaves MW, Camp RD. Arch Dermatol Res 1988;280 Suppl:S33-41. Institute of Dermatology, St. Thomas's Hospital, London, UK.

Albini, A, Iwamoto, Y, Kleinman. HK. Martin, GR, Aaronson, SA, Kozlowski, JM and McEwan. RN (1987) "A rapid in vitro assay for quantitating the invasive potential of tumor cells" *Cancer Res* 47(12):3239-45.

Beck, G, Yard, BA, Schulte, J, Oberacker. R. Van Ackern, K, Van Der Woude, FJ, Krimsky, M, Kaszkin, M and Yedgar, S (2002) "Inhibition of LPS-induced chemokine production in human lung endothelial cells by lipid conjugates anchored to the membrane" *Br J Pharmacol* 135(7):1665-74.

Cabanas. C and Hogg. N (1993) "Ligand intercellular adhesion molecule 1 has a necessary role in activation of integrin lymphocyte function-associated molecule 1" *Proc Natl Acad Sci U S A* 90(12):5838-42.

Dan, P, Dagan, A, Krimsky, M, Pruzanski. W. Vadas. P and Yedgar. S (1998) "Inhibition of type I and type II phospholipase A2 by phosphatidyl-ethanolamine linked to polymeric carriers" *Biochemistry* 37(17):6199-204.

Greaves MW and Camp RD (1988) "Prostaglandins. leukotrienes. phospholipase. platelet activating factor, and cytokines: an integrated approach to inflammation of human skin" *Arch Dermatol Res* 280:S33-41.

Krimsky, M. Dagan, A, Aptekar, L, Ligumsky, M and Yedgar. S (2000) "Assessment of intestinal permeability in rats by permeation of inulin-fluorescein" *J Basic Clin Physiol Pharmacol* 11(2):143-53.

Krimsky, M, Yedgar, S, Aptekar. L, Schwob. O. Goshen, G. Gruzman, A, Sasson, S and Ligumsky, M (2003) "Amelioration of TNBS-induced colon inflammation in rats by phospholipase A2 inhibitor" *Am J Physiol Gastrointest Liver Physiol* 285(3):G586-92.

Murthy. SN, Cooper, HS, Shim, H, Shah, RS, Ibrahim, SA and Sedergran, DJ (1993) "Treatment of dextran sulfate sodium-induced murine colitis by intracolonic cyclosporin" *Dig Dis Sci* 38(9):1722-34.

Okayasu, I, Hatakeyama. S. Yamada. M, Ohkusa, T, Inagaki, Y and Nakaya, R (1990) "A novel method in the induction of reliable experimental acute and chronic ulcerative colitis in mice" *Gastroenterology* 98(3):694-702.

Schnitzer. E. Dagan, A, Krimsky, M, Lichtenberg. D, Pinchuk, I, Shinar, H and Yedgar. S (2000) "Interaction of hyaluronic acid-linked phosphatidylethanotamine (HyPE) with LDL and its effect on the susceptibility of LDL lipids to oxidation" *Chem Phys Lipids* 104(2):149-60.

Schnitzer. E. Pinchuk. I. Fainaru, M, Lichtenberg, D and Yedgar, S (1998) "LDL-associated phospholipase A does not protect LDL against lipid peroxidation in vitro" *Free Radic Biol Med* 24(7-8)1294-303.

Schnitzer, E, Yedgar, S, Danino, D, Talmon. Y and Lichtenberg, D (1999) "The Interaction of hyaluronic-phosphatidylethanolamine with low density lipoprotein (LDL) and its effect on copper induced LDL oxidation" *Biophysical Journal* 76(1): Part 2.

Yard. BA. Yedgar. S. Scheele, M, Van Der Woude, D. Beck. G, Heidrich. B. Krimsky, M, Van Der Woude, FJ and Post. S (2002) "Modulation of IFN-gamma-induced immunogenicity by phosphatidylethanolamine-linked hyaluronic acid" *Transplantation* 73(6):984-92.

Yedgar, S, Lichtenberg. D and Schnitzer. E (2000) "Inhibition of phospholipase A(2) as a therapeutic target" *Biochim Biophys Acta* 1488(1-2):182-7.

Group V Phospholipase A2-mediated Oletic Acid Mobilization in Lipopolysaccharide-stimulated P388$D_1$ Macrophages; Balsinde Jesus, Balboa Maria A., Yedgar Saul, and Dennis Edward A., The Journal of Biological Chemistry, vol. 275, Feb. 18 pp. 4783-4786.

Inhibition of LPS-induced chemokine production in human lund endothelial cells by lipid conjugates achored to the membrane Beck, G. Ch, Yard B.A. Schulte J., Oberacker. R, Van Ackern K, Van Der Woude F.J, Krimsky M, Kaszkin M and Yedgar Y.; British Journal of Pharmacology (2002) 135, 1665-1674.

Control of capillary formation by membrane-anchored extracellular inhibitor of phospholipase $A_2$; Chem, W.M, Soria J, Coria C, Krimsky M and Yedgar S.; FEBS 26215 letters 522 (2002) 113-118.

Interaction of hyacluronic acid-linked phophatidylethonolmine (HyPE) with LDL and its effect on the susceptibility of LDL lips to oxidation; Schnitzer Edit, Dagan Arie, Krimsky Miron, Lichtenberg Dov, Pinchuk Ilya, Shinar Hadassa, Yedgar Saul; CPL 104 (2000) 149-160.

Inhibition of phopholipase A2 as a therapeutic target; Yedgar Saul, Lichtenberg Dov, Schnitzer Edit, BBA Biochimica et Biophyscia Acta 1488 (2000) 182-187.

Modulation of IFN-GAMMA-induced immunogenicity by phosphatidylethanolamine-linked hyaluronic acid; Yard Benito A., Yedgar Saul, Scheele Martin, Van Der Woulde Diane, Beck Grietje, Heidrich Barbel, Krimsky Miron,. Van Der Woulde Fokko J, and Post Stefan Transplantation vol. 73, 984-992, No. 6, Mar. 27, 2002.

Inhibition of Type I and Type II Phospholipase $A_2$ by Phosphatidyl-Ethanloamine Linked to Polymeric Carriers; Phyllis Dan, Arie Dagan, Miron Krimsky, Waldemar Pruzanski, Peter Vedas, and Saul Yedgar. Biochemistry 1998, 37, 6199-6204.

* cited by examiner ly. By the year 2030, approximately 70 million Americans will be over 65 years of age. Loss of vision among the elderly is a major health care problem: approximately one in three elderly persons has some form of vision-reducing eye disease by the age of 65. Vision impairment is associated with a decreased ability to perform activities of daily living and an increased risk for depression.

USE OF LIPID CONJUGATES IN THE TREATMENT OF DISEASES OR DISORDERS OF THE EYE

CROSS-REFERENCE TO RELATED APPLICATIONS

This application is a continuation-in-part of U.S. application Ser. No. 10/919,523, filed Aug. 17, 2004, which is a continuation-in-part of U.S. application Ser. No. 10/790,182, filed Mar. 2, 2004, now U.S. Pat. No. 7,141,552. This Application also claims the benefit of U.S. Provisional Application Ser. No. 60/858,706, filed Nov. 14, 2006 and U.S. Provisional Application Ser. No. 60/907,785, filed Apr. 17, 2007. All applications above are incorporated herein in their entirety.

FIELD OF THE INVENTION

This invention provides compounds and methods of use thereof for reducing the incidence, reducing the severity or pathogenesis, or treating a disease or disorder of the eye in a subject, including, inter alia, retinal detachment, macular degeneration, glaucoma or retinopathy, as well as contact lens solutions comprising said compounds.

BACKGROUND OF THE INVENTION

Compounds for use in the present invention are thought to inhibit the enzyme phospholipase A2 (PLA2, EC 3.1.1.4). Phospholipase A2 catalyzes the breakdown of phospholipids at the sn-2 position to produce a fatty acid and a lysophospholipid. The activity of this enzyme has been correlated with various cell functions, particularly with the production of lipid mediators such as eicosanoid production (prostaglandins, thromboxanes and leukotrienes), platelet activating factor and lysophospholipids. Compounds for use in the present invention may offer a wider scope of protection of cells and organisms from injurious agents and pathogenic processes, including the prevention and treatment of eye diseases.

The elderly population in the United States is increasing rapidly. By the year 2030, approximately 70 million Americans will be over 65 years of age. Loss of vision among the elderly is a major health care problem: approximately one in three elderly persons has some form of vision-reducing eye disease by the age of 65. Vision impairment is associated with a decreased ability to perform activities of daily living and an increased risk for depression.

Although estimates vary, there are approximately 10 million blind and visually impaired people in the United States, of which approximately 5.5 million are elderly individuals. Cataract, glaucoma, age-related macular degeneration, and diabetic retinopathy are the four eye disorders that pose the greatest threats to vision after age 40. Patients with age-related macular degeneration often have the following symptoms: blurred vision, image distortion, central scotoma, and/or difficulty reading; Patients with glaucoma often have the following symptoms: visual field loss and/or blurred vision (late); Patients with cataracts often complain of blurred vision, glare, and/or monocular diplopia; Patients with diabetic retinopathy often have the following symptoms: Blurred vision, floaters, visual field loss, often have poor night vision.

Other common eye disorders of aging, include presbyopia, dry eye, floaters and flashes, retinal detachment, and eyelid problems such as drooping upper or lower lids.

In the United States, diabetes is responsible for 8% of legal blindness, making it the leading cause of new cases of blindness in adults 20-74 years of age. Each year, between 12,000 to 24,000 people lose their sight because of diabetes, making patients with diabetes 25 times more likely to lose vision than those who are not diabetic, according to the American Academy of Opthalmology. In addition, diabetic retinopathy often leads to additional eye disorders such as retinal detachment, glaucoma cataract, and corneal disease, contributing to the high rate of blindness in diabetics.

Over 29 million people in the United States wear contact lenses, which provide a safe and effective way to correct vision when used with care and proper supervision. However, many contact lens wearers and potential contact lens wearers suffer from discomfort, dry eyes, and infection as a result of contact lens use. There is therefore a need to design contact lenses to comprise compounds that allow the lens to be more biocompatible, comfortable, tear-wettable, anti-bacterial and oxygen permeable.

SUMMARY OF THE INVENTION

In one embodiment, the invention provides a method of reducing the incidence, reducing the severity or pathogenesis of a disease or disorder of the eye in a subject comprising the step of contacting said subject with a compound comprising a lipid or phospholipid moiety bound optionally via a spacer to a physiologically acceptable monomer, dimer, oligomer, or polymer via an ester or amide bond, and/or a pharmaceutically acceptable salt or a pharmaceutical product thereof. In another embodiment, the invention provides a method of treating a disease or disorder of the eye in a subject comprising the step of contacting said subject with a compound comprising a lipid or phospholipid moiety bound optionally via a spacer to a physiologically acceptable monomer, dimer, oligomer, or polymer via an ester or amide bond, and/or a pharmaceutically acceptable salt or a pharmaceutical product thereof. In another embodiment, the invention provides a contact lens solution comprising a lipid or phospholipid moiety bound optionally via a spacer to a physiologically acceptable monomer, dimer, oligomer, or polymer via an ester or amide bond, and/or a pharmaceutically acceptable salt or a pharmaceutical product thereof.

In one embodiment, the compound for use in the solutions, compositions and methods of the present invention is represented by the structure of the general formula (A):

(A)

wherein
L is a lipid or a phospholipid;
Z is either nothing, ethanolamine, serine, inositol, choline, phosphate, or glycerol;
Y is either nothing or a spacer group ranging in length from 2 to 30 atoms;
X is a physiologically acceptable monomer, dimer, oligomer, or polymer; and
n is a number from 1 to 1000;
wherein any bond between L, Z, Y and X is either an amide or an esteric bond.

In one embodiment, the compound for use in the solutions, compositions and methods of the present invention is represented by the structure of the general formula (A):

(A)

wherein
L is a lipid or a phospholipid;
Z is either nothing, ethanolamine, serine, inositol, choline, phosphate, or glycerol;

Y is either nothing or a spacer group ranging in length from 2 to 30 atoms;

X is a physiologically acceptable monomer, dimer, oligomer, or polymer; and n is a number from 2 to 1000;

wherein any bond between L, Z, Y and X is either an amide or an esteric bond.

In another embodiment, the compound for use in the solutions, compositions and methods of the present invention is represented by the structure of the general formula (I):

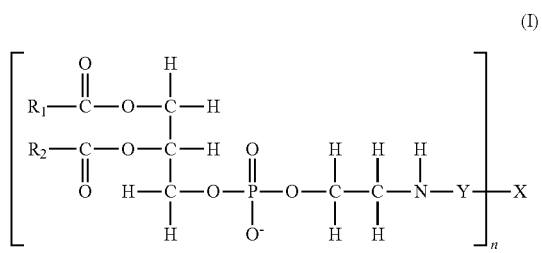

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is alginate, hydroxyethylstarch, polygeline, carboxymethylcellulose, or a combination thereof; and n is a number from 1 to 1000 or wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is alginate, hydroxyethylstarch, polygeline, carboxymethylcellulose, or a combination thereof; and n is a number from 1 to 1000.

In another embodiment, the compound for use in the solutions, compositions and methods of the present invention is represented by the structure of the general formula (I):

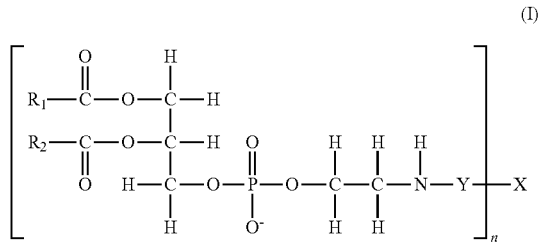

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is alginate, hydroxyethylstarch, polygeline, carboxymethylcellulose, or a combination thereof; and n is a number from 2 to 1000 or wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is alginate, hydroxyethylstarch, polygeline, carboxymethylcellulose, or a combination thereof; and n is a number from 2 to 1000.

DETAILED DESCRIPTION OF THE INVENTION

In one embodiment, the invention provides a method of reducing the incidence, reducing the severity or pathogenesis of a disease or disorder of the eye in a subject comprising the step of contacting said subject with a compound comprising a lipid or phospholipid moiety bound optionally via a spacer to a physiologically acceptable monomer, dimer, oligomer, or polymer via an ester or amide bond, and/or a pharmaceutically acceptable salt or a pharmaceutical product thereof.

In one embodiment, the invention provides a method of suppressing or inhibiting, a disease or disorder of the eye in a subject, comprising the step of contacting a cell with a compound comprising a lipid or phospholipid moiety bound to a physiologically acceptable monomer, dimer, oligomer, or polymer, and/or a pharmaceutically acceptable salt or a pharmaceutical product thereof.

In another embodiment, the invention provides a method of treating a disease or disorder of the eye in a subject, comprising the step of contacting said subject with a compound comprising a lipid or phospholipid moiety bound optionally via a spacer to a physiologically acceptable monomer, dimer, oligomer, or polymer via an ester or amide bond, and/or a pharmaceutically acceptable salt or a pharmaceutical product thereof.

In another embodiment, the invention provides a method of preventing a disease or disorder of the eye in a subject, comprising the step of contacting said subject with a compound comprising a lipid or phospholipid moiety bound optionally via a spacer to a physiologically acceptable monomer, dimer, oligomer, or polymer via an ester or amide bond, and/or a pharmaceutically acceptable salt or a pharmaceutical product thereof.

In one embodiment, the invention provides for the use of a lipid or phospholipid moiety bound optionally via a spacer to a physiologically acceptable monomer, dimer, oligomer, or polymer via an ester or amide bond, in the preparation of a composition for suppressing, inhibiting, preventing or treating a disease or disorder of the eye in a subject. In another embodiment, the invention provides for the use of a lipid or phospholipid moiety bound optionally via a spacer to a physiologically acceptable monomer, dimer, oligomer, or polymer via an ester or amide bond, in the preparation of a composition for reducing the incidence, reducing the severity or pathogenesis of a disease or disorder of the eye in a subject.

In one embodiment, the term "a disease or disorder of the eye" refers to any one or more of the following conditions: retinal detachment, macular edema, retinopathy, age-related macular degeneration, macular cyst, macular hole, solar retinopathy, diabetic retinopathy, branch retinal vein occlusion, or Lebers congenital amaurosis. In another embodiment, the term "a disease or disorder of the eye" refers to any one or more of the following conditions: corneal graft rejection, uveitis, inflammatory eye diseases, infectious eye diseases, ocular tumours, neovascular proliferative diseases, neovascular maculopathies, rheumatoid corneal melting disorders, or autoimmune disorders.

It is to be understood that the method of the present invention may be used to prevent or treat any disorder or disease of the eye or associated with the eye, or in another embodiment, any ophthalmic disorder. In one embodiment, the methods of the present invention may be used to prevent, suppress, inhibit or treat episcleritis, scleritis, or a combination thereof. In another embodiment, the methods of the present invention may be used to prevent, suppress, inhibit or treat retinopathy, including, inter alia, diabetic retinopathy, glaucoma, macular degeneration, retinal detachment, or a combination thereof. In another embodiment, the methods of the present invention may be used to prevent, suppress, inhibit or treat any one or more of the following diseases or disorders, or symptoms as a result thereof: achromatopsia/Maskun, amblyopia, anisometropia, Argyll Robertson pupil, astigmatism, anisometropia, blindness, chalazion, color blindness, achromatopsia/Maskun, esotropia, exotropia, floaters, vitreous detachment, Fuchs' dystrophy, hypermetropia, hyperopia, hypertensive retinopathy, iritis, keratoconus, Leber's congenital amaurosis, Leber's hereditary optic neuropathy, macular edema, myopia, nyctalopia, opthalmoplegia, including progressive external opthalmoplegia and internal opthalmoplegia, opthalmoparesis, presbyopia, pterygium, red eye (medicine), retinitis pigmentosa, retinopathy of prematurity, retinoschisis, river blindness, opthalmoplegia, scotoma, snow blindness/arc eye, eyelid disorders, ptosis, extraocular tumours, strabismus, which in one embodiment is esotropias, exotropias, vertical patterns, eye injuries, or a combination thereof. In another embodiment, the methods of the present invention may be used to prevent, suppress, inhibit or treat any one or more of the following diseases or disorders, or symptoms as a result thereof: neovascular glaucoma, retrolental fibroplasias, Vitamin A deficiency, contact lens overwear, atopic keratitis, superior limbic keratitis, pterygium keratitis sicca, Sjogrens syndrome, acne rosacea, phylectenulosis, syphilis, lipid degeneration, chemical burns, Mooren ulcer, Terrien's marginal degeneration, marginal keratolysis, polyarteritis, trauma, Wegeners sarcoidosis, scleritis, Steven's Johnson disease, periphigoid radial keratotomy, sickle cell anemia, syphilis, pseudoxanthoma elasticum, Paget's disease, vein occlusion, artery occlusion, carotid obstructive disease, chronic uveitis/vitritis, Lyme disease, systemic lupus erythematosis, Eales disease, Behcet's disease, presumed ocular histoplasmosis, Best's disease, optic pits, Stargardt's disease, pars planitis, chronic retinal detachment, retinoschisis, hyperviscosity syndromes, toxoplasmosis, trauma, post-laser complications, rubeosis, or a combination thereof.

In another embodiment, the methods of the present invention may be used in combination with or to prevent or treat secondary effects of: intraocular lens replacement; ophthalmic enucleation, evisceration, exenteration, or a combination thereof; lacrimal sac surgeries; corneal pterygium; lamellar keratoplasty; penetrating keratoplasty, or a combination thereof, as well as any of the disorders or conditions mentioned herein.

In one embodiment, the disease or disorder of the eye affects the anterior region of the eye, while in another embodiment, it affects the posterior region of the eye, while in another embodiment, it affects both the anterior and posterior regions of the eye. In one embodiment, the anterior segment includes the cornea, anterior chamber, iris and ciliary body (anterior choroid), posterior chamber and crystalline lens and the posterior segment includes the retina with optic nerve, choroid (posterior choroid) and vitreous. In one embodiment, eye disorders resulting from the pathologic conditions of structures in the anterior segment of the eye are dry eye syndrome, keratitis or corneal dystrophy, cataracts, and glaucoma. In one embodiment, the disease or disorders of the posterior segment of the eye in general are retinal or choroidal vascular diseases or hereditary diseases such as Lebers congenital amaurosis.

In one embodiment, "treating" refers to both therapeutic treatment and prophylactic or preventive measures, wherein the object is to prevent or lessen the targeted pathologic condition or disorder as described hereinabove. Thus, in one embodiment, treating may include suppressing, inhibiting, preventing, treating, or a combination thereof. Thus, in one embodiment, "treating" refers, inter alia, to increasing time to sustained progression, expediting remission, inducing remission, augmenting remission, speeding recovery, increasing efficacy of or decreasing resistance to alternative therapeutics, or a combination thereof. In one embodiment, "preventing" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers, inter alia, to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of an eye disease, while in one embodiment, "secondary" refers to a symptom that is derived from or consequent to a primary cause. In one embodiment, the compounds for use in the present invention treat primary or secondary symptoms or secondary complications related to an eye disease. In another embodiment, the compounds for use in the present invention treat primary or secondary symptoms or secondary complications related to an eye disease or disorder.

In another embodiment, "symptoms" may be any manifestation of a disease or pathological condition, comprising inflammation, swelling, fever, pain, bleeding, itching, runny nose, coughing, headache, migraine, dizziness, blurry vision, decreased visual acuity, light sensitivity, etc., or a combination thereof. In one embodiment, symptoms comprise itchy eyes, swollen eyelids, redness, irritation, watery eyes, mucoid discharge, pain, or a combination thereof.

Thus, in one embodiment of the present invention, the compounds for use in the present invention are directed towards the resolution of symptoms of a disease or disorder of the eye. In another embodiment, the compounds affect the pathogenesis underlying a disease or disorder of the eye.

In one embodiment, a disease or disorder of the eye may affect a cell, in one embodiment, a vertebrate cell, in another embodiment, a mammalian cell, and in another embodiment, a human cell. It is to be understood that compounds of the present invention may be efficacious in treating any cell type in which a disease or disorder of the eye or the causes of a disease or disorder of the eye may exert an effect. In one embodiment, a compound for use in the present invention may localize to or act on a specific cell type. In one embodiment, a compound for use in the present invention may be cytoprotective. In one embodiment a compound for use in the present invention may be inserted or partially inserted into a cell membrane. In another embodiment a compound for use in the present invention may be effective in treating a plurality of cell types.

In one embodiment, a disease or disorder of the eye is a primary or secondary symptom of an underlying illness, which in one embodiment, is an autoimmune disease. In one embodiment, the underlying illness is rheumatoid arthritis, systemic lupus erythematosus, Kawasaki's Disease, ulcerative colitis, Crohn's Disease, ankylosing spondylitis, Behcet's syndrome, psoriasis, Reiter's syndrome, sarcoidosis, diabetes, multiple sclerosis, etc., or any combination thereof.

In one embodiment, the methods of the present invention may be used to treat a disease or disorder of the eye in a subject that is immunosuppressed, while in another embodiment, in a subject that is immunodeficient, while in another embodiment, in a subject that is immunocompetent.

In another embodiment, the methods of the present invention may be used to prevent or treat glaucoma. In one embodiment, glaucoma is characterized by increased fluid pressure in the eye, which in one embodiment, is due to slowed fluid drainage from the eye. In one embodiment, glaucoma may damage the optic nerve and other parts of the eye, lead to vision loss or blindness, or a combination thereof. In one embodiment, glaucoma may refer to primary open angle glaucoma, normal pressure glaucoma, normal tension glaucoma, pigmentary glaucoma, pseudoexfoliation glaucoma, acute angle closure glaucoma, absolute glaucoma chronic glaucoma, congenital glaucoma, juvenile glaucoma, narrow angle glaucoma, chronic open angle glaucoma, simplex glaucoma, primary congenital glaucoma, secondary glaucoma, or a combination thereof.

In another embodiment, the methods of the present invention may be used to prevent or treat macular degeneration. In one embodiment, macular degeneration is characterized by damage to or breakdown of the macula, which in one embodiment, is a small area at the back of the eye. In one embodiment, macular degeneration causes a progressive loss of central sight, but not complete blindness. In one embodiment, macular degeneration is of the dry type, while in another embodiment, it is of the wet type. In one embodiment, the dry type is characterized by the thinning and loss of function of the macula tissue. In one embodiment, the wet type is characterized by the growth of abnormal blood vessels behind the macula. In one embodiment, the abnormal blood vessels hemorrhage or leak, resulting in the formation of scar tissue if untreated. In some embodiments, the dry type of macular degeneration can turn into the wet type. In one embodiment, macular degeneration is age-related, which in one embodiment is caused by an ingrowth of chorioidal capillaries through defects in Bruch's membrane with proliferation of fibrovascular tissue beneath the retinal pigment epithelium.

In another embodiment, the methods of the present invention may be used to prevent or treat retinopathy. In one embodiment, retinopathy refers to a disease of the retina, which in one embodiment is characterized by inflammation and in another embodiment, is due to blood vessel damage inside the eye. In one embodiment, retinopathy is diabetic retinopathy which, in one embodiment, is a complication of diabetes that is caused by changes in the blood vessels of the retina. In one embodiment, blood vessels in the retina leak blood and/or grow fragile, brush-like branches and scar tissue, which in one embodiment, blurs or distorts the images that the retina sends to the brain. In another embodiment, retinopathy is proliferative retinopathy, which in one embodiment, is characterized by the growth of new, abnormal blood vessels on the surface of the retina (neovascularization). In one embodiment, neovascularization around the pupil increases pressure within the eye, which in one embodiment, leads to glaucoma. In another embodiment, neovascularization leads to new blood vessels with weaker walls that break and bleed, or cause scar tissue to grow, which in one embodiment, pulls the retina away from the back of the eye (retinal detachment). In one embodiment, the pathogenesis of retinopathy is related to non-enzymatic glycation, glycoxidation, accumulation of advanced glycation end-products, free radical-mediated protein damage, up-regulation of matrix metalloproteinases, elaboration of growth factors, secretion of adhesion molecules in the vascular endothelium, or a combination thereof.

In one embodiment, retinopathy leads to macular edema, which in one embodiment, is swelling of the retina. In one embodiment, macular edema is characterized by retinal blood vessels that develop tiny leaks, which in one embodiment, allow blood and fluid to seep from the retinal blood vessels, and fatty material (called exudate) to deposit in the retina. In one embodiment, symptoms of macular edema comprise impaired or blurred vision.

In another embodiment, retinopathy refers to retinopathy of prematurity (ROP), which in one embodiment, occurs in premature babies when abnormal blood vessels and scar tissue grow over the retina. In one embodiment, retinopathy of prematurity is caused by a therapy necessary to promote the survival of a premature infant.

In another embodiment, retinopathy refers to arteriosclerotic retinopathy, which in one embodiment, is due to arteriosclerosis (hardening of the arteries). In another embodiment, retinopathy refers to hypertensive retinopathy, which in one embodiment, is due to high blood pressure. In another embodiment, retinopathy refers to solar retinopathy, while in another embodiment, it refers to drug-related retinopathy.

In another embodiment, the methods of the present invention may be used to prevent or treat retinal detachment, including, inter alia, rhegmatogenous, tractional, or exudative retinal detachment, which in one embodiment, is the separation of the retina from its supporting layers. In one embodiment, retinal detachment is associated with a tear or hole in the retina through which the internal fluids of the eye may leak. In one embodiment, retinal detachment is caused by trauma, the aging process, severe diabetes, an inflammatory disorder, neovascularization, or retinopathy of prematurity, while in another embodiment, it occurs spontaneously. In one embodiment, bleeding from small retinal blood vessels may cloud the vitreous during a detachment, which in one embodiment, may cause blurred and distorted images. In one embodiment, a retinal detachment can cause severe vision loss, including blindness.

Administration of the compounds for use in the present invention in a diversity of animal and cell models of disease invoke remarkable, and unexpected, cytoprotective effects, which are useful in the prevention and treatment of eye diseases and/or conditions.

In one embodiment of the present invention, the useful pharmacological properties of the compounds for use in the present invention, some of which are described hereinabove, may be applied for clinical use, and disclosed herein as methods for the prevention or treatment of a disease. The biological basis of these methods may be readily demonstrated by standard cellular and animal models of disease, for example, as described in the Examples hereinbelow.

In one embodiment, the pharmacological activities of compounds for use in the present invention, including membrane stabilization, anti-inflammation, anti-oxidant action, and attenuation of chemokine levels, may contribute to the resistance of a treated cell to diseases of the eye. In one embodiment, cell membrane stabilization may ameliorate or prevent tissue injury arising in the course of an eye disease. In another embodiment, anti-oxidant action may limit oxidative damage to cell and blood components arising in the course of an eye disease. In another embodiment, attenuation of chemokine levels may attenuate physiological reactions to stress that arise in the course of an eye disease.

In one embodiment of the invention, the compounds for use in the present invention described herein can be used to treat disease, through amelioration or prevention, of tissue injury arising in the course of pathological disease states by stabilizing cell membranes; limiting oxidative damage to cell and blood components; or attenuating physiological reactions to stress, as expressed in elevated chemokine levels.

In one embodiment, methods of the present invention involve treating a subject by, inter alia, controlling the expression, production, and activity of phospholipases such as PLA2; controlling the production and/or action of lipid mediators, such as eicosanoids, platelet activating factor (PAF) and lyso-phospholipids; amelioration of damage to cell surface glycosaminoglycans (GAG) and proteoglycans; controlling the production of oxidants, oxygen radicals and nitric oxide; protection of cells, tissues, and plasma lipoproteins from damaging agents, such as reactive oxygen species (ROS) and phospholipases; controlling the expression, production, and activity of cytokines, chemokines and interleukins; anti-oxidant therapy; anti-endotoxin therapy or any combination thereof.

In one embodiment of the invention, the term "controlling" refers to inhibiting the production and action of the above mentioned factors in order to maintain their activity at the normal basal level and suppress their activation in pathological conditions.

In one embodiment of the invention, eye disease is characterized by the presence of damaging agents, which comprise, inter alia, phospholipases, reactive oxygen species (ROS), free radicals, lysophospholipids, fatty acids or derivatives thereof, hydrogen peroxides, phospholipids, oxidants, cationic proteins, streptolysins, proteases, hemolysins, or sialidases.

Dosages and Routes of Administration

This invention encompasses administration of compounds as described herein or compositions comprising the same, for treating diseases of the eye.

In one embodiment, compositions of this invention are pharmaceutically acceptable. In one embodiment, the term "pharmaceutically acceptable" refers to any formulation which is safe, and provides the appropriate delivery for the desired route of administration of an effective amount of at least one compound for use in the present invention. This term refers to the use of buffered formulations as well, wherein the pH is maintained at a particular desired value, ranging from pH 4.0 to pH 9.0, in accordance with the stability of the compounds and route of administration.

In some embodiments, any of the compositions of this invention will comprise a lipid conjugate, in any form or embodiment as described herein. In some embodiments, any of the compositions of this invention will consist of a lipid conjugate, in any form or embodiment as described herein. In some embodiments, of the compositions of this invention will consist essentially of a lipid conjugate, in any form or embodiment as described herein. In some embodiments, the term "comprise" refers to the inclusion of the indicated active agent, such as the Compounds I-C, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

In one embodiment, a compound used in the methods of this invention may be administered alone or within a composition. In another embodiment, compositions comprising compounds for use in the present invention in admixture with conventional excipients, i.e. pharmaceutically acceptable organic or inorganic carrier substances suitable for parenteral, enteral (e.g. oral) or topical application which do not deleteriously react with the active compounds may be used. In one embodiment, suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. In another embodiment, the pharmaceutical preparations can be sterilized and if desired mixed with auxiliary agents, e.g. lubricants, preservatives, stabilizers, wetting agents, emulsifiers, salts for influencing osmotic pressure, buffers, coloring, flavoring and/or aromatic substances and the like which do not deleteriously react with the active compounds. In another embodiment, they can also be combined where desired with other active agents, e.g. vitamins.

In one embodiment, the therapeutic compositions of the instant invention comprise a compound of the instant invention and additional compounds effective in preventing or treating eye disease. In one embodiment, the additional compounds comprise anti-inflammatory compositions, which in one embodiment are non-steroidal anti-inflammatory medications, antihistamines, antibiotics, corticosteroids, cromolyn sodium (sodium cromoglicate), mast-cell stabilizers, artificial tears, lubricants, or a combination thereof. In one embodiment, antibiotics comprise chloramphenicol, fusidic acid, tetracycline, erythromycin, gentamycin, or a combination thereof. In another embodiment, an additional compound is vitamin A.

In one embodiment, the therapeutic compositions of the instant invention are administered with other treatments that relieve symptoms. In one embodiment, other treatments comprise application of cold compresses, while in another embodiment, warm compresses.

In one embodiment, the route of administration may be parenteral, enteral, or a combination thereof. In another embodiment, the route may be intra-ocular, topical, transdermal, intradermal, subcutaneous, intraperitoneal, intravenous, intra-arterial, vaginal, rectal, intratumoral, parcanceral, transmucosal, intramuscular, intravascular, intraventricular, intracranial, inhalation, nasal aspiration (spray), sublingual, oral, aerosol or suppository or a combination thereof. In one embodiment, the dosage regimen will be determined by skilled clinicians, based on factors such as exact nature of the condition being treated, the severity of the condition, the age and general physical condition of the patient, etc.

For intra-ocular application, eye drops, ointments, lotions, creams, or coated eye patches may be used in one embodiment. In another embodiment, intra-ocular application may comprise the use of contact lens comprising the compounds of the instant invention.

In one embodiment, intra-ocular application is used to treat an eye condition or disease. In another embodiment, intra-ocular injection is used to treat an eye condition or disease. In one embodiment, compounds may be administered intravitreally, in another embodiment, subretinally, while in another embodiment, intra-retinally, while in another embodiment, periocularly. In one embodiment, compounds may be administered intracamerally into the anterior chamber or vitreous, via a depot attached to the intraocular lens implant inserted during surgery, or via a depot placed in the eye sutured in the anterior chamber or vitreous.

For parenteral application, particularly suitable are injectable, sterile solutions, preferably oily or aqueous solutions, as well as suspensions, emulsions, or implants, including suppositories and enemas. Ampoules are convenient unit dosages. Such a suppository may comprise any agent described herein.

For application by inhalation, solutions or suspensions of the compounds mixed and aerosolized or nebulized in the presence of the appropriate carrier suitable. Such an aerosol may comprise any agent described herein and, in one embodiment, may be used to treat diseases or conditions caused by airborne pathogens, which may in one embodiment, cause sinusitis or upper respiratory infections, in addition to eye diseases.

For topical application, particularly in the area around the eye, an admixture of the compounds with conventional creams, lotions, or delayed release patches is acceptable. Such a cream or lotion may comprise any agent described herein, and, in one embodiment, may be used to treat an eye disease.

For enteral application, particularly suitable are tablets, dragees, liquids, drops, or capsules. A syrup, elixir, or the like can be used when a sweetened vehicle is employed.

Sustained or directed release compositions can be formulated, e.g. liposomes or those wherein the active compound is protected with differentially degradable coatings, e.g. by microencapsulation, multiple coatings, etc. It is also possible to freeze-dry the new compounds and use the lyophilisates obtained, for example, for the preparation of products for injection.

Thus, in one embodiment, the route of administration may be directed to an organ or system that is affected by an eye disease. For example, compounds may be administered in intra-ocular form to treat an eye disease. In another embodiment, the route of administration may be directed to a different organ or system than the one that is affected by an eye disease. For example, compounds may be administered parenterally to treat an eye disease. Thus, the present invention provides for the use of compounds of the instant invention in various dosage forms suitable for administration using any of the routes listed hereinabove.

In general, the doses utilized for the above described purposes will vary, but will be in an effective amount to exert the desired effect. As used herein, the term "pharmaceutically effective amount" refers to an amount of a compound of formulae A and I-LXXXVII as described hereinbelow, which will produce the desired alleviation in symptoms or other desired phenotype in a patient. The doses utilized for any of the above-described purposes will generally be from 1 to about 1000 milligrams per kilogram of body weight (mg/kg), administered one to four times per day, or by continuous IV infusion. When the compositions are dosed topically or intraocularly, they will generally be in a concentration range of from 0.1 to about 10% w/v, administered 1-4 times per day.

In one embodiment of the invention, the concentrations of the compounds will depend on various factors, including the nature of the condition to be treated, the condition of the patient, the route of administration and the individual tolerability of the compositions.

It will be appreciated that the actual preferred amounts of active compound in a specific case will vary according to the specific compound being utilized, the particular compositions formulated, the mode of application, and the particular conditions and organism being treated. Dosages for a given host can be determined using conventional considerations, e.g. by customary comparison of the differential activities of the subject compounds and of a known agent, e.g. by means of an appropriate, conventional pharmacological protocol.

In one embodiment, the compounds of the invention may be administered acutely for acute treatment of temporary conditions, or may be administered chronically, especially in the case of progressive, recurrent, or degenerative disease. In one embodiment, one or more compounds of the invention may be administered simultaneously, or in another embodiment, they may be administered in a staggered fashion. In one embodiment, the staggered fashion may be dictated by the stage or phase of the disease.

In one embodiment, the present invention offers methods for the treatment of disease based upon administration of lipids covalently conjugated through their polar head group to a physiologically acceptable chemical moiety, which may be of high or low molecular weight.

The present invention has been illustrated in terms of the anti-disease activity of compounds for use in the present invention and methods of their use as pharmaceutical compositions in the treatment of disease. The following sections present some examples of the therapeutic compounds for use in the present invention and their chemical preparation.

Compounds

In one embodiment, the compounds for use in the present invention or for the compositions of the present invention comprise a lipid or phospholipid moiety bound to a physiologically acceptable monomer, dimer, oligomer, or polymer. In one embodiment, the physiologically acceptable monomer, dimer, oligomer, or polymer is salicylate, salicylic acid, aspirin, a monosaccharide, lactobionic acid, maltose, an amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate, a dipeptide, a disaccharide, a trisaccharide, an oligosaccharide, a polysaccharide, a heteropolysaccharide, a homo-polysaccharide, a polypyranose, an oligopeptide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid, a glycosaminoglycan, polygeline ('haemaccel'), alginate, hydroxyethyl starch (hetastarch), polyethylene glycol, polycarboxylated polyethylene glycol, chondroitin-6-sulfate, chondroitin-4-sulfate, keratin, keratin sulfate, heparan sulfate, dermatin, dermatan sulfate, carboxymethylcellulose, heparin, dextran, or hyaluronic acid.

In one embodiment, examples of polymers which can be employed as the conjugated moiety for producing compounds for use in the present invention for use in the methods of this invention may be physiologically acceptable polymers, including water-dispersible or -soluble polymers of various molecular weights and diverse chemical types, mainly natural and synthetic polymers, such as glycosaminoglycans, hyaluronic acids, heparin, heparin sulfates, chondroitin sulfates, chondroitin-6-sulfates, chondroitin-4-sulfates, keratins, keratin sulfates, dermatins, dermatan sulfates, dextrans, plasma expanders, including polygeline ("Haemaccel", degraded gelatin polypeptide cross-linked via urea bridges, produced by "Behring"), "hydroxyethylstarch" (Hetastarch, HES) and extrans, food and drug additives, soluble cellulose derivatives (e.g. methylcellulose, carboxymethylcellulose), polyaminoacids, hydrocarbon polymers (e.g. polyethylene), polystyrenes, polyesters, polyamides, polyethylene oxides (e.g. polyethyleneglycols, polycarboxyethyleneglycols, polycarboxylated polyethyleneglycols), polyvinnylpyrrolidones, polysaccharides, polypyranoses, alginates, assimilable gums (e.g. xanthan gum), peptides, injectable blood proteins (e.g. serum albumin), cyclodextrin, and derivatives thereof.

In one embodiment, examples of monomers, dimers, and oligomers which can be employed as the conjugated moiety for producing compounds for use in the present invention for use in the methods of the invention may be mono- or disaccharides, trisaccharides, oligopeptides, carboxylic acids, dicarboxylic acids, fatty acids, dicarboxylic fatty acids, salicylates, slicyclic acids, acetyl salicylic acids, aspirins, lactobionic acids, maltoses, amino acids, glycines, glutaric acids, succinic acids, dodecanoic acids, didodecanoic acids, bile acids, cholic acids, cholesterylhemisuccinates, and di- and trisaccharide unit monomers of polysaccharides, polypyranoses, and/or glycosaminoglycans including heparins, heparan sulfates, hyaluronic acids, chondroitins, chondroitin sulfates, chondroitin-6-sulfates, chondroitin-4-sulfates, dermatins, dermatan sulfates, keratins, keratan sulfates, or dextrans.

In one embodiment, the lipid compounds for use in the present invention are described by the general formula:

[phosphatidylethanolamine-Y]$n$-X

[phosphatidylserine-Y]$n$-X

[phosphatidylcholine-Y]$n$-X

[phosphatidylinositol-Y]$n$-X

[phosphatidylglycerol-Y]$n$-X

[phosphatidic acid-Y]$n$-X

[lyso-phospholipid-Y]$n$-X

[diacyl-glycerol-Y]$n$-X

[monoacyl-glycerol-Y]$n$-X

[sphingomyelin-Y]$n$-X

[sphingosine-Y]$n$-X

[ceramide-Y]$n$-X wherein
Y is either nothing or a spacer group ranging in length from 2 to 30 atoms; and X is a physiologically acceptable monomer, dimer, oligomer or polymer; and
n is the number of lipid molecules bound to a molecule of X, wherein n is a number from 1 to 1000. In another embodiment, n is a number from 2 to 1000.

In one embodiment, the invention provides low-molecular weight compounds, previously undisclosed and unknown to possess pharmacological activity, of the general formula described hereinabove. In another embodiment, wherein the general formula described hereinabove describes low-molecular weight compounds, X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisacharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, or hyaluronic acid.

In one embodiment of this invention, X is any of the physiologically acceptable monomer, dimer, oligomer, or polymer, as described herein. In one embodiment, X is conjugated to the lipid, phospholipid, or spacer via an ester bond. In another embodiment, X is conjugated to the lipid, phospholipid, or spacer via an amide bond.

As defined by the structural formulae provided herein for the compounds for use in the present invention, these compounds may contain between one to one thousand lipid moieties bound to a single physiologically acceptable polymer molecule. In one embodiment of this invention, n is a number from 1 to 1000. In another embodiment, n is a number from 1 to 500. In another embodiment, n is a number from 1 to 100. In another embodiment, n is a number from 1 to 50. In another embodiment, n is a number from 1 to 25. In another embodiment, n is a number from 1 to 10. In another embodiment, n is a number from 1-5. In another embodiment, n is a number from 1 to 4. In another embodiment, n is a number from 1 to 3, In another embodiment, n is a number from 1 to 2. In another embodiment, n is a number from 2 to 1000. In another embodiment, n is a number from 2 to 100. In another embodiment, n is a number from 2 to 200. In another embodiment, n is a number from 2 to 50. In another embodiment, n is a number from 2 to 25. In another embodiment, n is a number from 2-10. In another embodiment, n is a number from 2 to 5. In another embodiment, n is a number from 2 to 4, In another embodiment, n is a number from 2 to 3. In another embodiment, n is a number from 3 to 300. In another embodiment, n is a number from 10 to 400. In another embodiment, n is a number from 50 to 500. In another embodiment, n is a number from 100 to 300. In another embodiment, n is a number from 300 to 500. In another embodiment, n is a number from 500 to 800. In another embodiment, n is a number from 500 to 1000.

In one embodiment of the invention, when the conjugated moiety is a polymer, the ratio of lipid moieties covalently bound may range from one to one thousand lipid residues per polymer molecule, depending upon the nature of the polymer and the reaction conditions employed. For example, the relative quantities of the starting materials, or the extent of the reaction time, may be modified in order to obtain products with either high or low ratios of lipid residues per polymer, as desired.

In one embodiment, the set of compounds comprising phosphatidylethanolamine covalently bound to a physiologically acceptable monomer, dimmer, oligomer, or polymer, is referred to herein as the PE-conjugates. In one embodiment, the phosphatidylethanolamine moiety is dipalmitoyl phosphatidylethanolamine. In another embodiment, the phosphatidylethanolamine moiety is dimyristoyl phosphatidylethanolamine. In another embodiment, related derivatives, in which either phosphatidylserine, phosphatidylcholine, phosphatidylinositol, phosphatidic acid or phosphatidylglycerol are employed in lieu of phosphatidylethanolamine as the lipid moiety provide equivalent therapeutic results, based upon the biological experiments described below for the compounds for use in the present invention and the structural similarities shared by these compounds.

In another embodiment, the lipid or phospholipid moiety is phosphatidic acid, an acyl glycerol, monoacylglycerol, diacylglycerol, triacylglycerol, sphingosine, sphingomyelin, chondroitin-4-sulfate, chondroitin-6-sulfate, ceramide, phosphatidylethanolamine, phosphatidylserine, phosphatidylcholine, phosphatidylinositol, or phosphatidylglycerol, or an ether or alkyl phospholipid derivative thereof.

In one embodiment, derivatives relevant to this invention are compounds wherein at least one of the fatty acid groups of the lipid moieties at position C1 or C2 of the glycerol backbone are substituted by a long chain alkyl group attached by amide, ether or alkyl bonds, rather than ester linkages.

In the methods, according to embodiments of the invention, the compounds for use in the present invention administered to the subject are comprised from at least one lipid moiety covalently bound through an atom of the polar head group to a monomeric or polymeric moiety (referred to herein as the conjugated moiety) of either low or high molecular weight. When desired, an optional bridging moiety can be used to link the compounds for use in the present invention moiety to the monomer or polymeric moiety. The conjugated moiety may be a low molecular weight carboxylic acid, dicarboxylic acid, fatty acid, dicarboxylic fatty acid, acetyl salicylic acid, cholic acid, cholesterylhemisuccinate, or mono- or di-saccharide, an amino acid or dipeptide, an oligopeptide, a glycoprotein mixture, a di- or trisaccharide monomer unit of a glycosaminoglycan such as a repeating unit of heparin, heparan sulfate, hyaluronic acid, chondroitin-sulfate, dermatan, keratan sulfate, or a higher molecular weight peptide or oligopeptide, a polysaccharide, a hetero-polysaccharide, a homo-polysaccharide, a polypyranose, polyglycan, protein, glycosaminoglycan, or a glycoprotein mixture. The composition of some phospholipid-conjugates of high molecular weight, and associated analogues, are the subject of U.S. Pat. No. 5,064,817, which is incorporated herein in its entirety by reference.

In one embodiment, the term "moiety" means a chemical entity otherwise corresponding to a chemical compound, which has a valence satisfied by a covalent bond.

In some cases, according to embodiments of the invention, the monomer or polymer chosen for preparation of the compound may in itself have select biological properties. For example, both heparin and hyaluronic acid are materials with known physiological functions. In the present invention, however, the compounds for use in the present invention formed from these substances as starting materials display a new and wider set of pharmaceutical activities than would be predicted from administration of either heparin or hyaluronic acid which have not been bound by covalent linkage to a phospholipid. In some embodiments, phosphatidylethanolamine (PE) linked to hyaluronic acid (Compound XXII), to heparin (Compound XXIV), to chondroitin sulfate A (Compound XXV), to carboxymethylcellulose (Compound XXVI), to Polygeline (haemaccel) (Compound XXVII), to alginate (Compound LI), or to hydroxyethylstarch (Compound XXVIII), are useful for methods and in compositions as herein described but perform unexpectedly in terms of potency and range of useful pharmaceutical activity compared to the free conjugates. Thus, the combination of a phospholipid such as phosphatidylethanolamine, or related phospholipids which differ with regard to the polar head group, such as phosphatidylserine (PS), phosphatidylcholine (PC), phosphatidylinositol (PI), and phosphatidylglycerol (PG), results in the formation of a compound which has novel pharmacological properties when compared to the starting materials alone. In one embodiment, such properties may include: greater lubrication, greater local persistence, greater anti-inflammatory properties, greater antioxidant activity, or a combination thereof.

The biologically active compounds for use in the present invention described herein can have a wide range of molecular weights, e.g. above 50,000 (up to a few hundred thousands) when it is desirable to retain the lipid conjugate in the vascular system and below 50,000 when targeting to extravascular systems is desirable. The sole limitation on the molecular weight and the chemical structure of the conjugated moiety is that it does not result in a compound devoid of the desired biological activity, or lead to chemical or physiological instability to the extent that the Compound is rendered useless as a drug in the method of use described herein.

In one embodiment, the compound for use in the present invention is represented by the structure of the general formula (A):

(A)

wherein
L is a lipid or a phospholipid;
Z is either nothing, ethanolamine, serine, inositol, choline, phosphate, or glycerol;
Y is either nothing or a spacer group ranging in length from 2 to 30 atoms;
X is a physiologically acceptable monomer, dimer, oligomer, or polymer; and
n is a number from 1 to 1000;
wherein any bond between L, Z, Y and X is either an amide or an esteric bond.

In one embodiment, the compound for use in the present invention is represented by the structure of the general formula (A):

(A)

wherein
L is a lipid or a phospholipid;
Z is either nothing, ethanolamine, serine, inositol, choline, phosphate, or glycerol;
Y is either nothing or a spacer group ranging in length from 2 to 30 atoms;
X is a physiologically acceptable monomer, dimer, oligomer, or polymer; and
n is a number from 2 to 1000;
wherein any bond between L, Z, Y and X is either an amide or an esteric bond.

In one embodiment, L is phosphatidyl, Z is ethanolamine, wherein L and Z are chemically bonded resulting in phosphatidylethanolamine, Y is nothing, and X is carboxymethylcellulose. In another embodiment, L is phosphatidyl, Z is ethanolamine, wherein L and Z are chemically bonded resulting in phosphatidylethanolamine, Y is nothing, and X is a glycosaminoglycan. In one embodiment, the phosphatidylethanolamine moiety is dipalmitoyl phosphatidylethanolamine. In another embodiment, the phosphatidylethanolamine moiety is dimyristoyl phosphatidylethanolamine.

In another embodiment, the compound for use in the present invention is represented by the structure of the general formula (I):

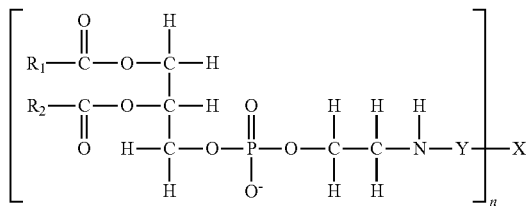

(I)

wherein
- $R_1$ is a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Y is either nothing or a spacer group ranging in length from 2 to 30 atoms; and
- X is either a physiologically acceptable monomer, dimer, oligomer or a physiologically acceptable polymer; and
- n is a number from 1 to 1,000;
- wherein if Y is nothing the phosphatidylethanolamine is directly linked to X via an amide bond and if Y is a spacer, the spacer is directly linked to X via an amide or an esteric bond and to the phosphatidylethanolamine via an amide bond.

In another embodiment, the compound for use in the present invention is represented by the structure of the general formula (I):

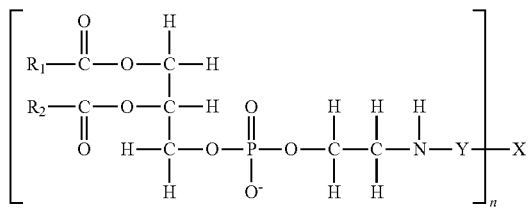

(I)

wherein
- $R_1$ is a linear, saturated, mono-unsaturated, or poly-unsaturated, alkyl chain ranging in length from 2 to 30 carbon atoms;
- $R_2$ is a linear, saturated, mono-unsaturated, or poly-unsaturated, alkyl chain ranging in length from 2 to 30 carbon atoms;
- Y is either nothing or a spacer group ranging in length from 2 to 30 atoms; and
- X is either a physiologically acceptable monomer, dimer, oligomer or a physiologically acceptable polymer; and
- n is a number from 2 to 1,000;
- wherein if Y is nothing the phosphatidylethanolamine is directly linked to X via an amide bond and if Y is a spacer, the spacer is directly linked to X via an amide or an esteric bond and to the phosphatidylethanolamine via an amide bond.

In one embodiment, compounds for use in the methods of the invention comprise one of the following as the conjugated moiety X: acetate, butyrate, glutarate, succinate, dodecanoate, didodecanoate, maltose, lactobionic acid, dextran, alginate, aspirin, cholate, cholesterylhemisuccinate, carboxymethyl-cellulose, heparin, hyaluronic acid, chondroitin sulfate, polygeline (haemaccel), hydroxyethylstarch (Hetastarch, HES) polyethyleneglycol, polycarboxylated polyethylene glycol, a glycosaminoglycan, a polysaccharide, a hetero-polysaccharide, a homo-polysaccharide, or a polypyranose. The polymers used as starting material to prepare the PE-conjugates may vary in molecular weight from 1 to 2,000 kDa.

Examples of phosphatidylethanolamine (PE) moieties are analogues of the phospholipid in which the chain length of the two fatty acid groups attached to the glycerol backbone of the phospholipid varies from 2-30 carbon atoms length, and in which these fatty acids chains contain saturated and/or unsaturated carbon atoms. In lieu of fatty acid chains, alkyl chains attached directly or via an ether linkage to the glycerol backbone of the phospholipid are included as analogues of PE. In one embodiment, the PE moiety is dipalmitoyl-phosphatidyl-ethanolamine. In another embodiment, the PE moiety is dimyristoyl-phosphatidyl-ethanolamine.

Phosphatidyl-ethanolamine and its analogues may be from various sources, including natural, synthetic, and semi-synthetic derivatives and their isomers.

Phospholipids which can be employed in lieu of the PE moiety are N-methyl-PE derivatives and their analogues, linked through the amino group of the N-methyl-PE by a covalent bond; N,N-dimethyl-PE derivatives and their analogues linked through the amino group of the N,N-dimethyl-PE by a covalent bond, phosphatidylserine (PS) and its analogues, such as palmitoyl-stearoyl-PS, natural PS from various sources, semi-synthetic PSs, synthetic, natural and artifactual PSs and their isomers. Other phospholipids useful as conjugated moieties in this invention are phosphatidylcholine (PC), phosphatidylinositol (PI), phosphatidic acid and phosphoatidylglycerol (PG), as well as derivatives thereof comprising either phospholipids, lysophospholipids, phosphatidic acid, sphingomyelins, lysosphingomyelins, ceramide, and sphingosine.

For PE-conjugates and PS-conjugates, the phospholipid is linked to the conjugated monomer or polymer moiety through the nitrogen atom of the phospholipid polar head group, either directly or via a spacer group. For PC, PI, and PG conjugates, the phospholipid is linked to the conjugated monomer or polymer moiety through either the nitrogen or one of the oxygen atoms of the polar head group, either directly or via a spacer group.

In another embodiment, the compound for use in the present invention is represented by the structure of the general formula (II):

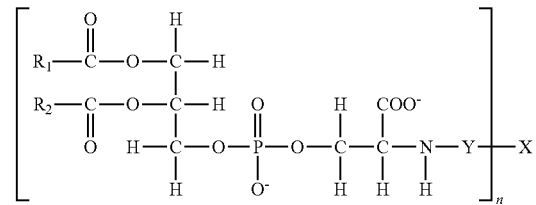

(II)

wherein
- $R_1$ is a linear, saturated, mono-unsaturated, or poly-unsaturated, alkyl chain ranging in length from 2 to 30 carbon atoms;

R₂ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a glycosaminoglycan; and n is a number from 1 to 1000;

wherein if Y is nothing, the phosphatidylserine is directly linked to X via an amide bond and if Y is a spacer, the spacer is directly linked to X via an amide or an esteric bond and to the phosphatidylserine via an amide bond.

In another embodiment, the compound for use in the present invention is represented by the structure of the general formula (II):

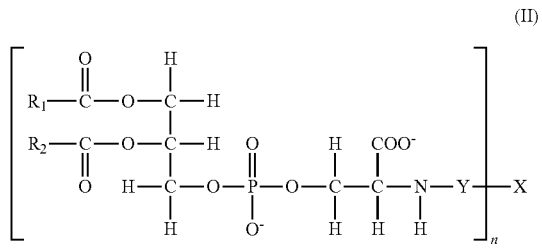

(II)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a glycosaminoglycan; and n is a number from 2 to 1000;

wherein if Y is nothing, the phosphatidylserine is directly linked to X via an amide bond and if Y is a spacer, the spacer is directly linked to X via an amide or an esteric bond and to the phosphatidylserine via an amide bond.

In one embodiment, the phosphatidylserine may be bonded to Y, or to X if Y is nothing, via the COO⁻ moiety of the phosphatidylserine.

In another embodiment, the compound for use in the present invention is represented by the structure of the general formula (III):

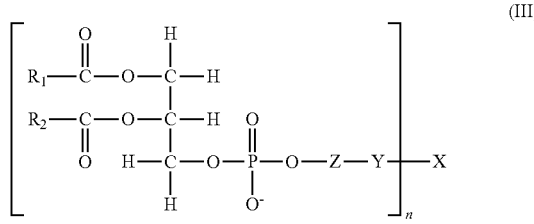

(III)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 1 to 1000;

wherein any bond between the phosphatidyl, Z, Y and X is either an amide or an esteric bond.

In another embodiment, the compound for use in the present invention is represented by the structure of the general formula (IV):

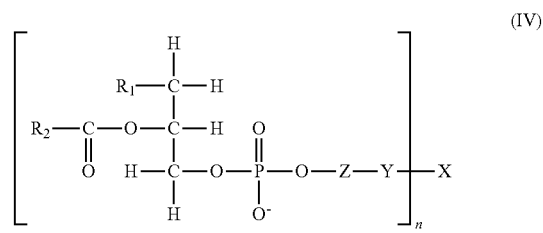

(IV)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (III):

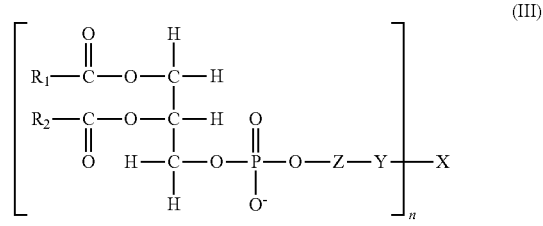

(III)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 2 to 1000;

wherein any bond between the phosphatidyl, Z, Y and X is either an amide or an esteric bond.

In another embodiment, the compound for use in the present invention is represented by the structure of the general formula (IV):

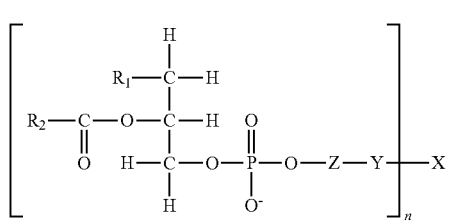

(IV)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (IV):

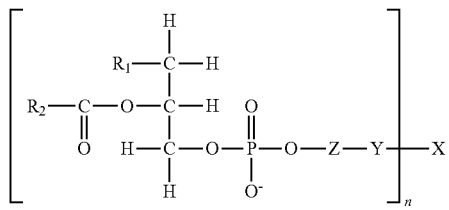

(IV)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 2 to 1000;

wherein any bond between the phospholipid, Z, Y and X is either an amide or an esteric bond.

In another embodiment, the compound for use in the present invention is represented by the structure of the general formula (V):

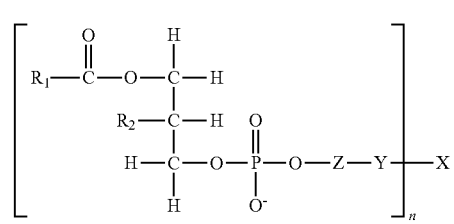

(V)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (V):

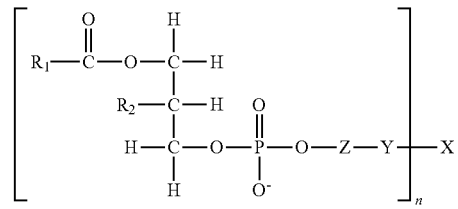

(V)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 2 to 1000;

wherein any bond between the phospholipid, Z, Y and X is either an amide or an esteric bond.

In another embodiment, the compound for use in the present invention is represented by the structure of the general formula (VI):

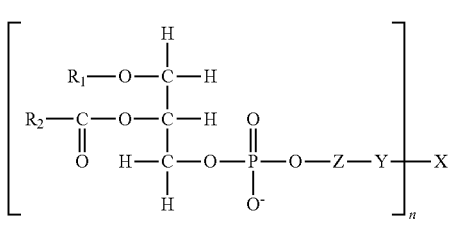

(VI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (VI):

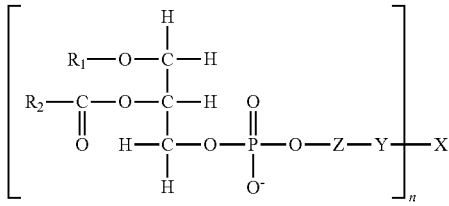

(VI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 2 to 1000;

wherein any bond between the phospholipid, Z, Y and X is either an amide or an esteric bond.

In another embodiment, the compound for use in the present invention is represented by the structure of the general formula (VII):

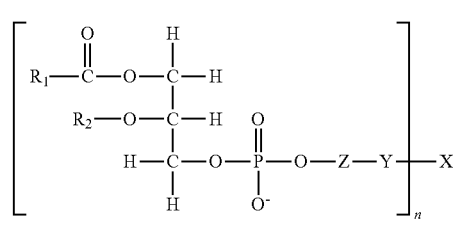

(VII)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (VII):

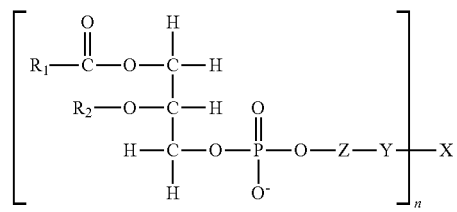

(VII)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In one embodiment of the invention, phosphatidylcholine (PC), phosphatidylinositol (PI), phosphatidic acid (PA), wherein Z is nothing, and phosphatidylglycerol (PG) conjugates are herein defined as compounds of the general formula (III).

In another embodiment, the compound for use in the present invention is represented by the structure of the general formula (VIII):

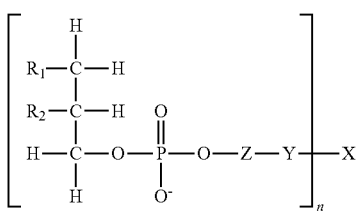

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (VIII):

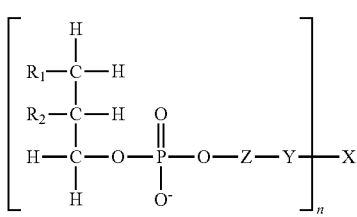

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 2 to 1000;

wherein any bond between the phospholipid, Z, Y and X is either an amide or an esteric bond.

In another embodiment, the compound for use in the present invention is represented by the structure of the general formula (IX):

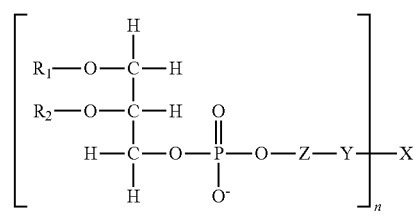

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (IX):

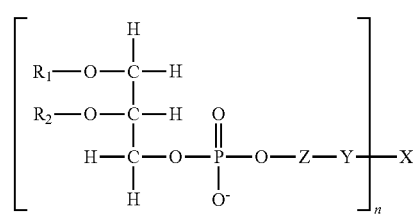

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 2 to 1000;

wherein any bond between the phospholipid, Z, Y and X is either an amide or an esteric bond.

In another embodiment, the compound for use in the present invention is represented by the structure of the general formula (IXa):

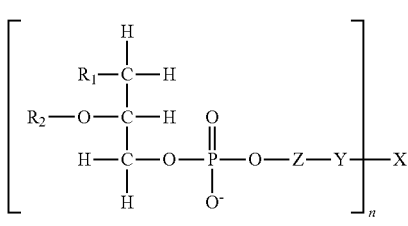

(IXa)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (IXa):

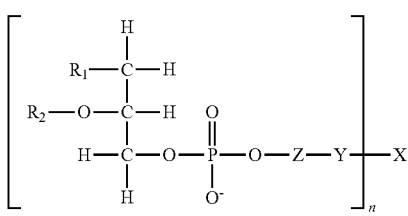

(IXa)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 2 to 1000;

wherein any bond between the phospholipid, Z, Y and X is either an amide or an esteric bond.

In another embodiment, the compound for use in the present invention is represented by the structure of the general formula (IXb):

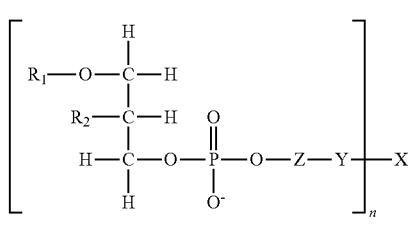

(IXb)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 1 to 1000;

wherein any bond between the phospholipid, Z, Y and X is either an amide or an esteric bond.

In another embodiment, the compound for use in the present invention is represented by the structure of the general formula (IXb):

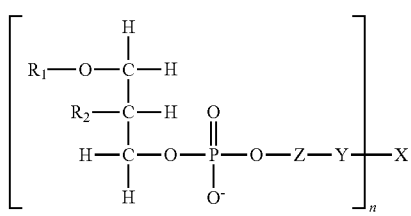

(IXb)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 2 to 1000;

wherein any bond between the phospholipid, Z, Y and X is either an amide or an esteric bond.

In another embodiment, the compound for use in the present invention is represented by the structure of the general formula (X):

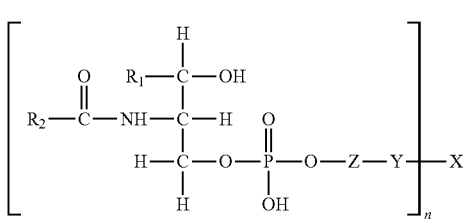

(X)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 1 to 1000;

wherein any bond between the ceramide phosphoryl, Z, Y and X is either an amide or an esteric bond.

In another embodiment, the compound for use in the present invention is represented by the structure of the general formula (X):

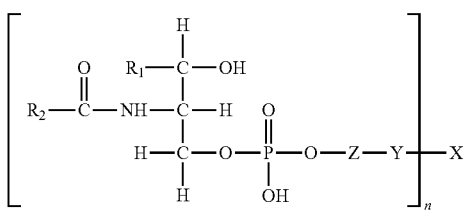

(X)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 2 to 1000;

wherein any bond between the ceramide phosphoryl, Z, Y and X is either an amide or an esteric bond.

In another embodiment, the compound for use in the present invention is represented by the structure of the general formula (XI):

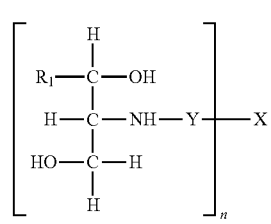

(XI)

wherein $R_1$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a glycosaminoglycan; and n is a number from 1 to 1000;

wherein if Y is nothing the sphingosyl is directly linked to X via an amide bond and if Y is a spacer, the spacer is directly linked to X and to the sphingosyl via an amide bond and to X via an amide or an esteric bond.

In another embodiment, the compound for use in the present invention is represented by the structure of the general formula (XI):

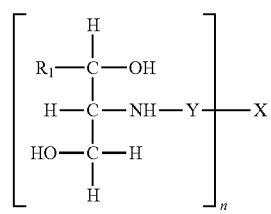

(XI)

wherein $R_1$ is a linear, saturated, mono-unsaturated, or poly-unsaturated, alkyl chain ranging in length from 2 to 30 carbon atoms;

Y is either nothing or a spacer group ranging in length from 2 to 30 atoms;

X is a glycosaminoglycan; and n is a number from 2 to 1000;

wherein if Y is nothing the sphingosyl is directly linked to X via an amide bond and if Y is a spacer, the spacer is directly linked to X and to the sphingosyl via an amide bond and to X via an amide or an esteric bond.

In another embodiment, the compound for use in the present invention is represented by the structure of the general formula (XII):

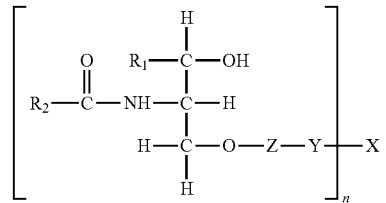

(XII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 1 to 1000;

wherein any bond between the ceramide, Z, Y and X is either an amide or an esteric bond.

In another embodiment, the compound for use in the present invention is represented by the structure of the general formula (XII):

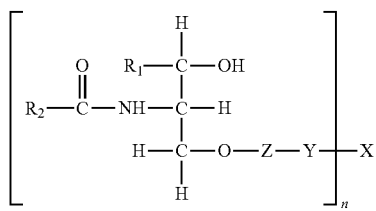

(XII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, ethanolamine, serine, inositol, choline, or glycerol;

Y is either nothing or a spacer group ranging in length from 2 to 30 atoms;

X is a glycosaminoglycan; and n is a number from 2 to 1000;

wherein any bond between the ceramide, Z, Y and X is either an amide or an esteric bond.

In another embodiment, the compound for use in the present invention is represented by the structure of the general formula (XIII):

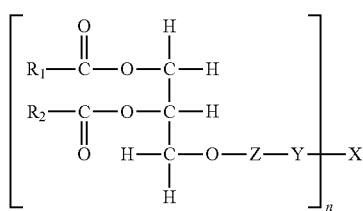

(XIII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the diglyceryl, Z, Y and X is either an amide or an esteric bond.

In another embodiment, the compound for use in the present invention is represented by the structure of the general formula (XIII):

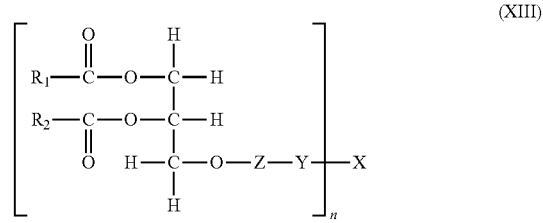

(XIII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 2 to 1000;

wherein any bond between the diglyceryl, Z, Y and X is either an amide or an esteric bond.

In another embodiment, the compound for use in the present invention is represented by the structure of the general formula (XIV):

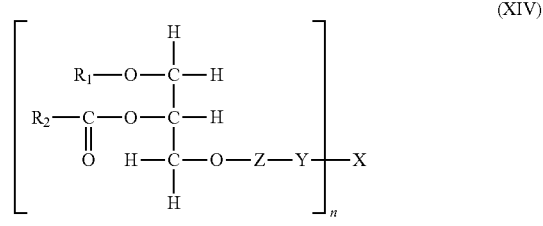

(XIV)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

x is a glycosaminoglycan; and n is a number from 1 to 1000;

wherein any bond between the glycerolipid, Z, Y and X is either an amide or an esteric bond.

In another embodiment, the compound for use in the present invention is represented by the structure of the general formula (XIV):

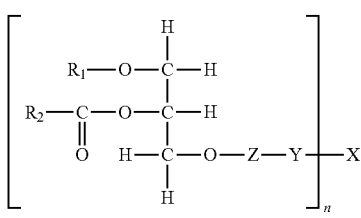

(XIV)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 2 to 1000;

wherein any bond between the glycerolipid, Z, Y and X is either an amide or an esteric bond.

In another embodiment, the compound for use in the present invention is represented by the structure of the general formula (XV):

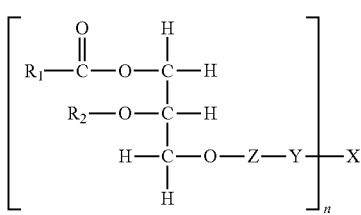

(XV)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the glycerolipid, Z, Y and X is either an amide or an esteric bond.

In another embodiment, the compound for use in the present invention is represented by the structure of the general formula (XV):

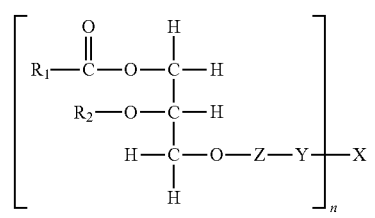

(XV)

wherein $R_1$ is a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 2 to 1000;

wherein any bond between the glycerolipid, Z, Y and X is either an amide or an esteric bond.

In another embodiment, the compound for use in the present invention is represented by the structure of the general formula (XVI):

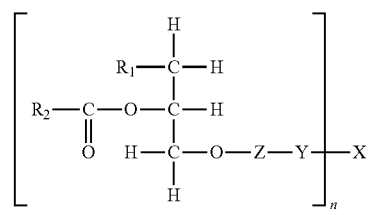

(XVI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XVI):

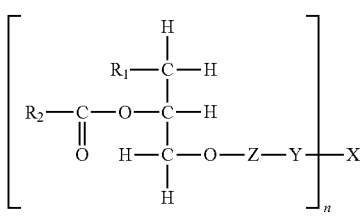

(XVI)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 2 to 1000;

wherein any bond between the lipid, Z, Y and X is either an amide or an esteric bond.

In another embodiment, the compound for use in the present invention is represented by the structure of the general formula (XVII):

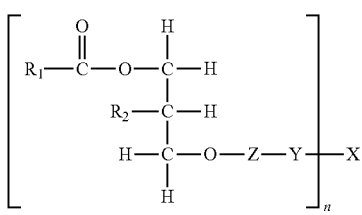

(XVII)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XVII):

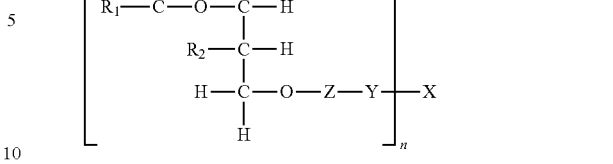

(XVII)

wherein $R_1$ is either hydrogen or a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 2 to 1000;

wherein any bond between the lipid, Z, Y and X is either an amide or an esteric bond.

In another embodiment, the compound for use in the present invention is represented by the structure of the general formula (XVIII):

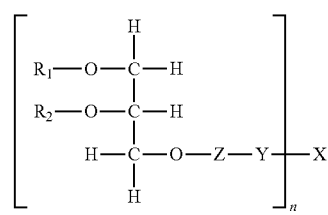

(XVIII)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XVIII):

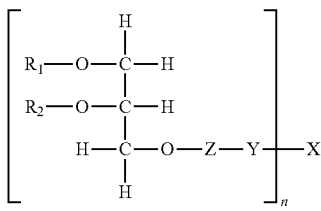

(XVIII)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 2 to 1000;

wherein any bond between the lipid, Z, Y and X is either an amide or an esteric bond.

In another embodiment, the compound for use in the present invention is represented by the structure of the general formula (XIX):

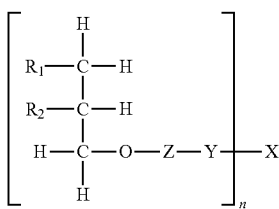

(XIX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XIX):

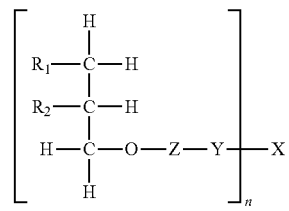

(XIX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XX):

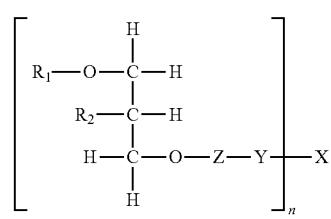

(XX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XX):

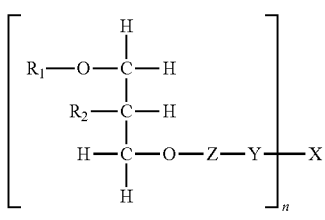

(XX)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 2 to 1000;

wherein any bond between the lipid, Z, Y and X is either an amide or an esteric bond.

In another embodiment, the compound for use in the present invention is represented by the structure of the general formula (XXI):

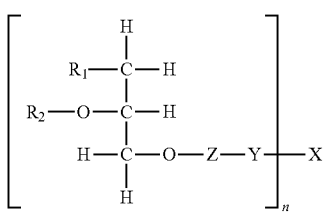

(XXI)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 1 to 1000;

wherein any bond between the lipid, Z, Y and X is either an amide or an esteric bond.

In another embodiment, the compound for use in the present invention is represented by the structure of the general formula (XXI):

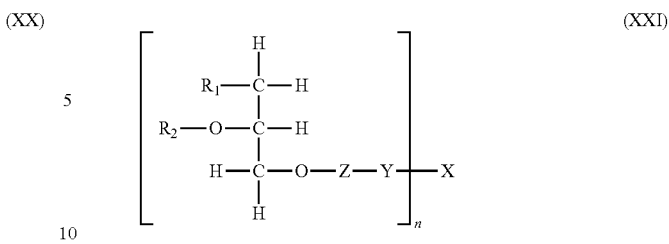

(XXI)

wherein $R_1$ is either hydrogen or a linear, saturated, mono-unsaturated, or poly-unsaturated, alkyl chain ranging in length from 2 to 30 carbon atoms;

$R_2$ is either hydrogen or a linear, saturated, mono-unsaturated, or poly-unsaturated, alkyl chain ranging in length from 2 to 30 carbon atoms;

Z is either nothing, choline, phosphate, inositol, or glycerol;

Y is either nothing or a spacer group ranging in length from 2 to 30 atoms;

X is a glycosaminoglycan; and n is a number from 2 to 1000;

wherein any bond between the lipid, Z, Y and X is either an amide or an esteric bond.

For any or all of the compounds represented by the structures of the general formulae (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), and (XXII) hereinabove: In one embodiment, X is a glycosaminoglycan. According to this aspect and in one embodiment, the glycosaminoglycan may be, inter alia, hyaluronic acid, heparin, heparan sulfate, chondroitin sulfate, keratin, keratan sulfate, dermatan sulfate or a derivative thereof. In another embodiment, X is not a glycosaminoglycan. In another embodiment, X is a polysaccharide, which in one embodiment is a hetero-polysaccharide, and in another embodiment, is a homo-polysaccharide. In another embodiment, X is a polypyranose.

In another embodiment, the glycosaminoglycan is a polymer of disaccharide units. In another embodiment, the number of the disaccharide units in the polymer is m. In another embodiment, m is a number from 2-10,000. In another embodiment, m is a number from 2-500. In another embodiment, m is a number from 2-1000. In another embodiment, m is a number from 50-500. In another embodiment, m is a number from 2-2000. In another embodiment, m is a number from 500-2000. In another embodiment, m is a number from 1000-2000. In another embodiment, m is a number from 2000-5000. In another embodiment, m is a number from 3000-7000. In another embodiment, m is a number from 5000-10,000. In another embodiment, a disaccharide unit of a glycosaminoglycan may be bound to one lipid or phospholipid moiety. In another embodiment, each disaccharide unit of the glycosaminoglycan may be bound to zero or one lipid or phospholipid moieties. In another embodiment, the lipid or phospholipid moieties are bound to the —COOH group of the disaccharide unit. In another embodiment, the bond between the lipid or phospholipid moiety and the disaccharide unit is an amide bond.

In one embodiment, the invention encompasses compounds, compositions and preparations, comprising a phospholipid-GAG conjugate, whereby the molar ratio in the compounds, compositions and preparations between the phospholipid and the GAG is in the range of between 1.5:1 to 20:1, or in another embodiments, 2:1 to 10:1, or in another embodiment, 3:1 to 7:1, or in another embodiment, 1.5:1 to 7:1. In another embodiment, the molar ratio between the phospholipid and the GAG is in the range of between 2:1 to 10:1. In another embodiment, the molar ratio between the phospholipid and the GAG is in the range of between 2:1 to 5:1. In another embodiment, the molar ration between the phospholipid and the GAG is 2:1. In another embodiment, the molar ration between the phospholipid and the GAG is 3:1. In another embodiment, the molar ration between the phospholipid and the GAG is 5:1. In another embodiment, the molar ration between the phospholipid and the GAG is 10:1. In another embodiment, the molar ration between the phospholipid and the GAG is 20:1.

In one embodiment, the compound of the present invention comprises a glycosaminoglycan (GAG) with a molecular weight in the range of between 30-100 kD. In another embodiment, the GAG has a molecular weight in the range of between 30-80 kD. In another embodiment, the GAG has a molecular weight in the range of between 30-50 kD. In another embodiment, the GAG has a molecular weight in the range of between 20-80 kD. In another embodiment, the GAG has a molecular weight in the range of between 20-50 kD.

In another embodiment, the chondroitin sulfate may be, inter alia, chondroitin-6-sulfate, chondroitin-4-sulfate or a derivative thereof.

In one embodiment of the invention, Y is nothing. Non-limiting examples of suitable divalent groups forming the optional bridging group (which in one embodiment, is referred to as a spacer) Y, according to embodiments of the invention, are straight or branched chain alkylene, e.g. of 2 or more, preferably 4 to 30 carbon atoms, —CO-alkylene-CO, —NH-alkylene-NH—, —CO-alkylene-NH—, —NH-alkylene-NH, CO-alkylene-NH—, an amino acid, cycloalkylene, wherein alkylene in each instance, is straight or branched chain and contains 2 or more, preferably 2 to 30 atoms in the chain, —(—O—CH(CH$_3$)CH$_2$—)$_x$— wherein x is an integer of 1 or more.

According to embodiments of the invention, in addition to the traditional phospholipid structure, related derivatives for use in this invention are phospholipids modified at the C1 or C2 position to contain an amine, ether or alkyl bond instead of an ester bond. In one embodiment of the invention, the alkyl phospholipid derivatives and ether phospholipid derivatives are exemplified herein.

In one embodiment of the invention, the sugar rings of the glycosaminoglycan are intact. In another embodiment, intact refers to closed. In another embodiment, intact refers to natural. In another embodiment, intact refers to unbroken.

In one embodiment of the invention, the structure of the lipid or phospholipid in any compound according to the invention is intact. In another embodiment, the natural structure of the lipid or phospholipids in any compound according to the invention is maintained.

In one embodiment, the compounds for use in the present invention are biodegradable.

In one embodiment, the compound according to the invention is phosphatidylethanolamine bound to aspirin. In one embodiment, the compound according to the invention is phosphatidylethanolamine bound to glutarate.

In some embodiments, the compounds for use are as listed in Table 1 below.

TABLE 1

| Phospholipid | Spacer | Polymer (m.w.) | Compound |
| --- | --- | --- | --- |
| PE | None | Hyaluronic acid (2-2000 kDa) | XXII |
| Dimyristoy1-PE | None | Hyaluronic acid | XXIII |
| PE | None | Heparin (0.5-110 kDa) | XXIV |
| PE | None | Chondroitin sulfate A | XXV |
| PE | None | Carboxymethylcellulose (20-500 kDa) | XXVI |
| PE | Dicarboxylic acid + Diamine | Polygeline (haemaccel) (4-40 kDa) | XXVII |
| PE | None | Hydroxyethylstarch | XXVIII |
| PE | Dicarboxylic acid + Diamine | Dextran (1-2,000 kDa) | XXIX |
| PE | None | Aspirin | XXX |
| PE | Carboxyl amino group | Hyaluronic acid (2-2000 kDa) | XXXI |
| PE | Dicarboxyl group | Hyaluronic acid (2-2000 kDa) | XXXII |
| PE | Dipalmitoic acid | Hyaluronic acid (2-2000 kDa) | XXXIII |
| PE | Carboxyl amino group | Heparin (0.5-110 kDa) | XXXIV |
| PE | Dicarboxyl group | Heparin (0.5-110 kDa) | XXXV |
| PE | Carboxyl amino group | Chondroitin sulfate A | XXXVI |
| PE | Dicarboxyl group | Chondroitin sulfate A | XXXVII |
| PE | Carboxyl amino group | Carboxymethylcellulose (20-500 kDa) | XXXVIII |
| PE | Dicarboxyl group | Carboxymethylcellulose (20-500 kDa) | XXXIX |
| PE | None | Polygeline (haemaccel) (4-40 kDa) | XL |
| PE | Carboxyl amino group | Polygeline (haemaccel) (4-40 kDa) | XLI |

TABLE 1-continued

| Phospholipid | Spacer | Polymer (m.w.) | Compound |
| --- | --- | --- | --- |
| PE | Dicarboxyl group | Polygeline (haemaccel) (4-40 kDa) | XLII |
| PE | Carboxyl amino group | Hydroxyethylstarch | XLIII |
| PE | Dicarboxyl group | Hydroxyethylstarch | XLIV |
| PE | None | Dextran (1-2,000 kDa) | XLV |
| PE | Carboxyl amino group | Dextran (1-2,000 kDa) | XLVI |
| PE | Dicarboxyl group | Dextran (1-2,000 kDa) | XLVII |
| PE | Carboxyl amino group | Aspirin | XLVIII |
| PE | Dicarboxyl group | Aspirin | XLIX |
| PE | None | Albumin | L |
| PE | None | Alginate (2-2000 kDa) | LI |
| PE | None | Polyaminoacid | LII |
| PE | None | Polyethylene glycol | LIII |
| PE | None | Lactobionic acid | LIV |
| PE | None | Acetylsalicylate | LV |
| PE | None | Cholesteryl-hemmisuccinate | LVI |
| PE | None | Maltose | LVII |
| PE | None | Cholic acid | LVIII |
| PE | None | Chondroitin sulfates | LIX |
| PE | None | Polycarboxylated polyethylene glycol | LX |
| Dipalmitoyl-PE | None | Hyaluronic acid | LXI |
| Dipalmitoyl-PE | None | Heparin | LXII |
| Dipalmitoyl-PE | None | Chondroitin sulfate A | LXIII |
| Dipalmitoyl-PE | None | Carboxymethylcellulose | LXIV |
| Dipalmitoyl-PE | None | Polygeline (haemaccel) | LXV |
| Dipalmitoyl-PE | None | Hydroxyethylstarch | LXVI |
| Dipalmitoyl-PE | None | Dextran | LXVII |
| Dipalmitoyl-PE | None | Aspirin | LXVIII |
| Dimyristoyl-PE | None | Heparin | LXVIX |
| Dimyristoyl-PE | None | Chondroitin sulfate A | LXX |
| Dimyristoyl-PE | None | Carboxymethylcellulose | LXXI |
| Dimyristoyl-PE | None | Polygeline (haemaccel) | LXXII |
| Dimyristoyl-PE | None | Hydroxyethylstarch | LXXIII |
| Dimyristoyl-PE | None | Dextran | LXXIV |
| Dimyristoyl-PE | None | Aspirin | LXXV |
| PS | None | Hyaluronic acid | LXXVI |
| PS | None | Heparin | LXXVII |
| PS | None | Polygeline (haemaccel) | LXXVIII |
| PC | None | Hyaluronic acid | LXXIX |
| PC | None | Heparin | LXXX |
| PC | None | Polygeline (haemaccel) | LXXXI |
| PI | None | Hyaluronic acid | LXXXII |
| PI | None | Heparin | LXXXIII |
| PI | None | Polygeline (haemaccel) | LXXXIV |
| PG | None | Hyaluronic acid | LXXXV |
| PG | None | Heparin | LXXXVI |
| PG | None | Polygeline (haemaccel) | LXXXVII |
| PE | None | Glutaryl | LXXXVIII |
| Dipalmitoyl-PE | None | Alginate | LXXXIX |

TABLE 1-continued

| Phospholipid | Spacer | Polymer (m.w.) | Compound |
|---|---|---|---|
| Dimyristoyl-PE | None | Alginate | XC |
| PS | None | Alginate | XCI |
| PC | None | Alginate | XCII |
| PI | None | Alginate | XCIII |
| PG | None | Alginate | XCIV |
| PS | None | Hydroxyethylstarch | XCV |
| PC | None | Hydroxyethylstarch | XCVI |
| PI | None | Hydroxyethylstarch | XCVII |
| PG | None | Hydroxyethylstarch | XCVIII |
| PE | —CO—(CH$_2$)$_3$—CO—NH—(CH$_2$)$_6$— | Hydroxyethylstarch | XCIX |
| PE | —CO—CH$_2$— | Carboxymethylcellulose | C |

In one embodiment of the invention, the compounds for use in the present invention are any one or more of Compounds I-C. In another embodiment, the invention provides a composition comprising any combination of any of the compounds of the invention or the use of any combination of any of the compounds of the invention. In another embodiment, the invention provides a composition comprising Compounds XCIX, C, or a combination thereof and uses thereof. In another embodiment, the invention provides a composition comprising Compounds LXV, LXVI, LXXI, LXXII, LXXIII, LXXXIX, XC, or a combination thereof and uses thereof. In another embodiment, the compounds for use in the present invention are Compound XXII, Compound XXIII, Compound XXIV, Compound XXV, Compound XXVI, Compound XXVII, Compound XXVIII, Compound XXIX, Compound XXX, Compound LI, or pharmaceutically acceptable salts thereof, in combination with a physiologically acceptable carrier or solvent. According to embodiments of the invention, these polymers, when chosen as the conjugated moiety, may vary in molecular weights from 200 to 2,000,000 Daltons. In one embodiment of the invention, the molecular weight of the polymer as referred to herein is from 200 to 1000 Daltons. In another embodiment, the molecular weight of the polymer as referred to herein is from 200 to 1000 Daltons. In another embodiment, the molecular weight of the polymer as referred to herein is from 1000 to 5000 Daltons. In another embodiment, the molecular weight of the polymer as referred to herein is from 5000 to 10,000 Daltons. In another embodiment, the molecular weight of the polymer as referred to herein is from 10,000 to 20,000 Daltons. In another embodiment, the molecular weight of the polymer as referred to herein is from 10,000 to 50,000 Daltons. In another embodiment, the molecular weight of the polymer as referred to herein is from 20,000 to 70,000 Daltons. In another embodiment, the molecular weight of the polymer as referred to herein is from 50,000 to 100,000 Daltons. In another embodiment, the molecular weight of the polymer as referred to herein is from 100,000 to 200,000 Daltons. In another embodiment, the molecular weight of the polymer as referred to herein is from 200,000 to 500,000 Daltons. In another embodiment, the molecular weight of the polymer as referred to herein is from 200,000 to 1,000,000 Daltons. In another embodiment, the molecular weight of the polymer as referred to herein is from 500,000 to 1,000,000 Daltons. In another embodiment, the molecular weight of the polymer as referred to herein is from 1,000,000 to 2,000,000 Daltons. Various molecular weight species have been shown to have the desired biological efficacy.

In one embodiment, AlgPE has a molecular weight of approximately 120 kD, CSAPE has a molecular weight of approximately 100 kD, HemPE has a molecular weight of approximately 75 kD, HesDMPE has a molecular weight of approximately 90 kD, CMPE has a molecular weight of approximately 75 kD, or a combination thereof. In one embodiment, "approximately" refers to up to 5%, 10%, 15%, 20%, or 25% of the value. In another embodiment, "approximately" refers to 5-25%, 5-15%. 10-25%, 10-20%, 15-25% of the value.

In one embodiment of this invention, low molecular weight compounds for use in the present invention are defined hereinabove as the compounds of formula (I)-(XXI) wherein X is a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisacharide, or a di- or trisaccharide monomer unit of heparin, heparan sulfate, keratin, keratan sulfate, chondroitin, chondroitin-6-sulfate, chondroitin-4-sulfate, dermatin, dermatan sulfate, dextran, hyaluronic acid, glycosaminoglycan, or polypyranose.

Examples of suitable divalent groups forming the optional bridging group Y are straight- or branched-chain alkylene, e.g. of 2 or more, preferably 4 to 18 carbon atoms, —CO-alkylene-CO, —NH-alkylene-NH—, —CO-alkylene-NH—, cycloalkylene, wherein alkylene in each instance, is straight or branched chain and contains 2 or more, preferably 2 to 18 carbon atoms in the chain, —(—O—CH(CH$_3$)CH$_2$—)$_x$— wherein x is an integer of 1 or more.

In another embodiment, in addition to the traditional phospholipid structure, related derivatives for use in this invention are phospholipids modified at the C1 or C2 position to contain an ether or alkyl bond instead of an ester bond. These derivatives are exemplified hereinabove by the general formulae (VIII) and (IX).

In one embodiment of the invention, X is covalently conjugated to a lipid. In another embodiment, X is covalently conjugated to a lipid via an amide bond. In another embodiment, X is covalently conjugated to a lipid via an esteric bond. In another embodiment, the lipid is phosphatidylethanolamine.

In one embodiment, cell surface GAGs play a key role in protecting cells from diverse damaging agents and processes, such as reactive oxygen species and free radicals, endotoxins, cytokines, invasion promoting enzymes, and agents that induce and/or facilitate degradation of extracellular matrix and basal membrane, cell invasiveness, white cell extravasation and infiltration, chemotaxis, and others. In addition, cell surface GAGs protect cells from bacterial, viral and parasitic infection, and their stripping exposes the cell to interaction and subsequent internalization of the microorganism. Enrichment of cell surface GAGs would thus assist in protection of the cell from injurious processes. Thus, in one embodiment of the invention, PLA2 inhibitors are conjugated to GAGs or GAG-mimicking molecules. In another embodiment, these compounds for use in the present invention provide wide-range protection from diverse injurious processes, and are effective in amelioration of diseases that requires cell protection from injurious biochemical mediators.

In another embodiment, a GAG-mimicking molecule may be, inter alia, a negatively charged molecule. In another embodiment, a GAG-mimicking molecule may be, inter alia, a salicylate derivative. In another embodiment, a GAG-mimicking molecule may be, inter alia, a dicarboxylic acid.

In another embodiment, the invention provides a pharmaceutical composition for treating a subject suffering from an eye disease, including a lipid or phospholipid moiety bonded to a physiologically acceptable monomer, dimer, oligomer, or polymer; and a pharmaceutically acceptable carrier or excipient.

In another embodiment, the invention provides a pharmaceutical composition for treating a subject suffering from an eye disease, including any one of the compounds for use in the present invention or any combination thereof; and a pharmaceutically acceptable carrier or excipient. In another embodiment, the compounds for use in the present invention include, inter alia, the compounds represented by the structures of the general formulae as described hereinbelow: (A), (I), (II), (III), (IV), (V), (VI), (VII), (VIII), (IX), (IXa), (IXb), (X), (XI), (XII), (XIII), (XIV), (XV), (XVI), (XVII), (XVIII), (XIX), (XX), (XXI), (XXII), or any combination thereof.

The combination of lipids, such as, but not limited to phosphatidylethanolamine and phosphatidylserine, with additional monomer or polymer moieties, is thus a practical route to the production of new drugs for medical purposes, provided that the resultant chemical composition displays the desired range of pharmacological properties. In one embodiment, the compounds for use in the present invention possess a combination of multiple and potent pharmacological effects in addition to the ability to inhibit the extracellular form of the enzyme phospholipase A2. While the pharmacological activity of the compounds for use in the present invention described herein may be due in part to the nature of the lipid moiety, the multiple and diverse combination of pharmacological properties observed for the compounds for use in the present invention emerges from the ability of the compound structure to act essentially as several different drugs in one chemical entity.

In the cases described herein, the diversity of biological activities and the effectiveness in disease exhibited by the compounds for use in the present invention far exceed the properties anticipated by use of the starting materials themselves, when administered alone or in combination. However, the phospholipid conjugate compounds, alone or in combination, are valuable when used in the methods of treating diseases and conditions specifically described herein.

Eye Devices

It is to be understood that the compounds for use in the present invention may also be used in combination with any device which is applied to an eye surface or applied to the internal regions of the eye. In one embodiment, such a device is a contact lens, while in other embodiments, it is a corneal prosthetic device, prosthetic iris implant, scleral lens prosthetic device, an intra-ocular implant, a scleral buckle, ophthalmic tantalum clip, ophthalmic conformer, artificial eye, absorbable implant, eye sphere implant, extraocular orbital implant, keratoprosthesis, intraocular lens, scleral shell, eye valve implant, or a combination thereof.

In one embodiment, the present invention provides a substrate having a coating on at least a portion of a surface of said substrate, said coating comprising a lipid or phospholipid moiety bound to a physiologically acceptable monomer, dimer, oligomer, or polymer as any of the embodiments describe hereinabove. In one embodiment, the physiological acceptable monomer, dimer, oligomer, or polymer is a polypyranose. In one embodiment, the substrate is a contact lens. In one embodiment, the substrate is an implant. In one embodiment, the substrate is part of a device for ophthalmic or ophthamologic use.

In another embodiment, this invention provides a contact lens solution comprising the compounds of the instant invention. Contact lens solutions of the instant invention may comprise, inter alia, rewetting drops, cleaning solutions, washing solutions, storage solutions, packing solutions, saline solution, daily cleaner, multipurpose solution, hydrogen peroxide solution, or a combination thereof. Any solution which may be used for storage, preservation, or cleaning of a contact lens or lenses is considered to be an embodiment of this invention. The safety and tolerability of solutions comprising the subject compounds as comfort ingredients, for example, in contact lens packaging solutions, is exemplified in Example 6. In one embodiment, appliances for use with the lenses and/or solutions of this invention may be coated with the compounds for use in the instant invention as described herein, as well.

In one embodiment, contact lens solutions of the instant invention will additionally comprise surfactants, tonicity agents, viscosity builders, anti-microbials, buffering agents, or a combination thereof. In one embodiment, surfactants may be non-ionic, and in one embodiment may comprise poly(oxyethylene) and poly(oxypropylene), polyethylene glycol esters of fatty acids, e.g. coconut, polysorbate, polyoxyethylene or polyoxypropylene ethers of higher alkanes (C12-C18). Examples include Tween® 20 (polysorbate 20) and Tween® 80, polyoxyethylene (23) lauryl ether (Brij® 35), polyoxyethyene (40) stearate (Myrj® 52), polyoxyethylene (25) propylene glycol stearate (Atlas® G 2612).

An amphoteric, cationic or anionic surfactant may also be present in the contact lens solution. Amphoteric surfactants suitable for use in a composition according to the present invention include materials of the type are offered commercially under the trade name "Miranol". Another useful class of amphoteric surfactants are exemplified by cocoamidopropyl betaine commercially available under the trade name Amphoso CA. Surfactants suitable for use in the invention can be readily ascertained, in view of the foregoing description, from McCutcheon's Detergents and Emulsifiers, North American Edition, McCutcheon Division, MC Publishing Co., Glen Rock, N.J. 07452 and the CTFA International Cosmetic Ingredient Handbook, Published by The Cosmetic, Toiletry, and Fragrance Association, Washington, D.C.

The pH of some contact lens solutions should, in one embodiment, be maintained within the range of about 6.0 to 8.0, preferably about 6.5 to 7.8. Suitable buffers may be added, such as boric acid, sodium borate, potassium citrate, citric acid, sodium bicarbonate, TRIS and various mixed phosphate buffers (including combinations of $Na_2HPO_4$, $NaH_2PO_4$ and $KH_2PO_4$) and mixtures thereof. Generally, buffers will be used in amounts ranging from about 0.05 to 2.5 percent by weight, and preferably, from 0.1 to 1.5 percent. In one embodiment, the contact lens solutions of this invention contain a borate buffer, comprising one or more of boric acid, sodium borate, potassium tetraborate, potassium metaborate or mixtures of the same. Also, various buffer systems such as citrate, phosphate (appropriate mixtures of $Na_2HPO4$, $NaH_2PO4$, and $KH_2PO4$), bicarbonate, tromethamine and other appropriate nitrogen-containing buffers (such as ACES, BES, BICINE, BIS-Tris, BIS-Tris Propane, HEPES, HEPPS, imidazole, MES, MOPS, PIPES, TAPS, TES, Tricine) can be used to ensure a physiologic pH between about pH 6.5 and 8.5.

In one embodiment, the contact lens solutions of the present invention are also adjusted with tonicity agents, to approximate the osmotic pressure of normal lacrimal fluids which is equivalent to a 0.9 percent solution of sodium chloride or 2.5 percent of glycerol solution. The solutions are made substantially isotonic with physiological saline used alone or in combination. In another embodiment, propylene glycol, lactulose, trehalose, sorbitol, mannitol or other osmotic agents may also be added to replace some or all of the sodium chloride.

Examples of suitable tonicity-adjusting agents include, but are not limited to: sodium and potassium chloride, dextrose, glycerin, calcium and magnesium chloride. These agents are typically used individually in amounts ranging from about 0.01 to 2.5% (w/v) and preferably, from about 0.2 to about 1.5% (w/v). Preferably, the tonicity agent will be employed in an amount to provide a final osmotic value of 200 to 400 mOsm/kg, and more preferably between about 250 to about 350 mOsm/kg, and most preferably between about 280 to about 320 mOsm/kg.

It may also be desirable to optionally include water-soluble viscosity builders in the solutions of the present invention. Because of their demulcent effect, viscosity builders have a tendency to further enhance a lens wearer's comfort by means of a film on the lens surface cushioning impact against the eye. Included among the water-soluble viscosity builders are polymers like polyvinylalcohol cellulose-derived polymers, and povidone. In another embodiment, viscosity builders comprise polyethylene glycol, surfactants, polyvinylpyrrolidone, polyvinyl alcohol, carboxymethyl cellulose and similar materials. Such polymers may be used in an amount of from about 0.01 to about 4.0 weight percent or less. Surface-active agents, such as polysorbates, polyoxyethylenes and certain phosphonates, may be added to ensure proper wetting and/or cleaning. Sequestering agents such as ethylenediaminetetraacetic acid (EDTA), phosphonates, citrate, gluconate and tartarate, are also common additives to preservatives, disinfection or cleaning solutions.

In another embodiment, nitrogen (non-fluorocarbon) is used as a propellant in the contact lens solution.

In another embodiment, the contact lens solution of the instant invention further comprises anti-microbial compounds, which in one embodiment, comprise glycosides, alkaloids, phenolics (anthocyanins, quinones, flavonols and flavonoids, etc.), terpenoids (including phytosterols and carotenoids), or a combination thereof. In another embodiment, anti-microbial compounds comprise allicin, aucubin, berberine, bilberry extract, caffeic acid, chlorogenic acid, Echinacea extract, ferulic acid, hydrastine, lipoic acid, naringin, oleuropein, proanthocyanidins, quercetin, rutin, or a combination thereof, which in one embodiment are present in amounts of 10 to 10,000 parts per million. In another embodiment, saponins, can be used as natural plant surface-active or cleaning agents in lens solutions. Specifically, triterpenoid saponins and steriod saponins are particularly effective in contact lens or ophthalmic solutions. In another embodiment, the solution comprises benzyldimethyl {2-[2-(p-1,1,3,3-tetramethylbutylphenoxy)ethoxy]ethyl}ammonium chloride (BDT) as an anti-microbial compound.

In another embodiment, a contact lens solution of the instant invention comprises preservatives, which in one embodiment comprise thimerosal, edetate disodium, sorbic acid, polyaminopropyl biguanide, POLYQUAD (polyquartenium-1), EDTA, or a combination thereof.

In one embodiment, a contact lens solution may be a daily cleaner, which in one embodiment comprises cocoamphocarboxyglycinate, sodium lauryl sulfate, hexylene glycol, sodium chloride, sodium, Tween 21, microlens poloxamer 407, potassium chloride, poloxamine, isopropyl alchohol, amphoteric 10, or a combination thereof.

In one embodiment, contact lens solution may comprise an enzyme, which in one embodiment may be pancreatin, papain, subtilisin, or a combination thereof, which in one embodiment may be for removing protein from the lens.

In another embodiment, a device for use with contact lenses may comprise compounds for use in the instant invention. In one embodiment, such a device may be a standard device commercially available for the storage, cleaning, disinfection, and/or carriage of contact lenses, which in one embodiment, is characterized by a hollow well. In one embodiment, a single device may be suitable for storage, cleaning, disinfection, and/or carriage of contact lenses, while in another embodiment, each is a separate device.

In one embodiment, the substrate, which in one embodiment is a contact lens, contact lens device, contact lens solution and/or intraocular device, comprising compounds for use in the instant invention suppresses, inhibits, prevents or treats eye-related disorders, including, inter alia, those described hereinabove, in a subject. In another embodiment, the substrate comprising compounds for use in the instant invention prevents or treats proteinaceous deposits accumulating on the substrate. In another embodiment, the compounds for use in the instant invention endow the surface of the substrate with the property of being more hydrophilic, which in one embodiment, may increase comfort, decrease eye dryness, or a combination thereof. In another embodiment, the compounds for use in the instant invention prevent adverse reactions that are directly or indirectly related to the substrate, such as corneal edema, inflammation, or lymphocyte infiltration. In another embodiment, the substrate comprising compounds for use in the instant invention increases wettability, decreases adhesion, increases biocompatability, provides UV shielding, prevents glare, decreases dryness, grittiness, general discomfort, prevents microbial (in one embodiment, bacterial) infections, or a combination thereof or provides other desirable characteristics and properties to the substrate that are known in the Art.

Preparation of Compounds for Use in the Present Invention

In one embodiment, the preparation of high molecular weight compounds for use in the methods of the present invention is as described in U.S. Pat. No. 5,064,817, which is incorporated fully herein by reference. In one embodiment, these synthetic methods are applicable to the preparation of low molecular weight compounds for use in the present invention as well, i.e. compounds for use in the present invention comprising monomers and dimers as the conjugated moiety, with appropriate modifications in the procedure as would be readily evident to one skilled in the art. The preparation of some low molecular weight compounds for use in the present invention may be conducted using methods well known in the art or as described in U.S. patent application Ser. No. 10/952,496, which is incorporated herein by reference in its entirety.

Without further elaboration, it is believed that one skilled in the art can, using the preceding description, utilize the present invention to its fullest extent. The following preferred specific embodiments are, therefore, to be construed as merely illustrative, and not limiting the remainder of the disclosure in any way whatsoever.

EXAMPLES

The abbreviations used in the examples below are:
PE=phosphatidyl-ethanolamine
HA=hyaluronic acid
Cpd=Compound
Cpd XXII=dipalmitoyl-PE conjugated to HA
Cpd XXIII=dimyristoyl-phosphatidyl-ethanolamine linked to HA
Cpd XXIV=PE conjugated to heparin
Cpd XXV=PE conjugated to chondroitin sulfate A (CSA)
Cpd XXVI=PE conjugated to carboxymethyl cellulose (CMC)
Cpd XXVII=PE conjugated to Polygeline (haemaccel)
Cpd XXIX=PE conjugated to dextran
Cpd XXX=PE conjugated to aspirin
Cpd LXXXVIII=PE conjugated to glutaryl
Cpd LI=PE conjugated to alginate
The compounds used in the examples below were prepared as described in U.S. patent application Ser. No. 10/952, 496, which is fully incorporated herein by reference.

Example 1

Effect of Lipid Conjugates in an In Vitro Model of Diabetic Retinopathy

Human Retinal Endothelial Cell Culture

Human eyes from donors are obtained and human retinal endothelial cells (HRECs) are isolated. The identity of HRECs is validated by demonstrating endothelial cell incorporation of fluorescence-labeled, acetylated LDL, and by fluorescence-activated cell-sorting analysis. To determine the effect of high glucose, HRECs are grown for 7 days in normal (5.5 mM) or high (25 mM) D-glucose medium.

Bovine Retinal Endothelial Cell Culture

Isolated bovine retinas are homogenized in ice-cold Eagle's minimal essential medium (MEM) with HEPES by a Teflon-glass homogenizer and microvessels trapped on an 83 mm nylon mesh. Vessels are transferred into 2×MEM containing 500 µg/ml collagenase, 200 µg/ml pronase (BDH, Poole, UK) and 200 µg/ml DNase at 37° C. for 20 min. The resultant vessel fragments are trapped on 53 µm mesh, washed with cold MEM, and centrifuged at 225×g for 10 min. The pellet is suspended in microvascular endothelial cell basal medium (MECBM) with growth supplement (TCS Works Ltd., Buckingham, UK) at 37° C., 5% $CO_2$ for 3 days. Confluent cells are used between passages 1 and 3.

ELISA for VEGF

VEGF protein concentration is determined from retinal endothelial cell culture-conditioned medium using the Quantikine® Human VEGF Immunoassay ELISA kit (R & D Systems). Retinal endothelial cell culture are treated with either 5.5 or 25 mM glucose and aliquots are taken daily for analysis.

ELISA for IGF-I

IGF-I protein concentration is determined from retinal endothelial cell culture-conditioned medium using the Quantikine® Human IGF Immunoassay ELISA kit (R & D Systems). Retinal endothelial cell culture are treated with either 5.5 or 25 mM glucose and aliquots are taken daily for analysis.

Statistical Analysis

Data are analyzed using the Student's t-test and reported as mean±standard deviation (SD). A p value <0.05 is considered significant.

Treatment with 1, 5, and 10 µM, and other concentrations of Compounds XXII, XXIII, or XXV restore the levels of IGF-1 and VEGF in human and bovine retinal endothelial cell culture to the level of controls.

In another embodiment, other markers may be examined including ICAM-1, VCAM-1, HIF-1, transmembrane reductase (TMR), and EPO; pigment epithelium-derived factor (PEDF) in the eye, markers of oxidative stress including osmotic stress after accumulation of sorbitol, increased cytosolic NADH/NAD ratio, depletion of NADPH and accumulation of fructose with the resulting non-enzymatic production of advanced glycation end products (AGES); and/or ESR, fibrinogen, SDF/1_, RANTES, EpOx, Haptoglobin and ACE in peripheral blood. Antibodies are used to probe the GAG portion of the conjugate over a time course compared to unconjugated control, and show greater local persistence. In one embodiment, GAGs are tagged.

Example 2

Effect of Lipid Conjugates in an In Vivo Model of Diabetic Retinopathy

Diabetes is induced Long-Evans rats via ip streptozotocin (STZ) injections at 70-85 mg/kg, for 3 to 5 days. To help ease the transition to diabetes, the rats are given 10% sugar water for 24 hours post-STZ injection. Retinal photographs are taken and blood glucose tests are performed to determine baselines for each rat. The normal glucose range for a rat is 80-100 mg/dl.

Alternatively, C57BU6 mice (SLC, Shizuoka, Japan) are used. Postnatal day (P)7 mice with their nursing mothers are maintained for a full 5 days in 80% oxygen to generate the nonvascular retinal area. On P12, they are placed in normoxia for an additional 5 days to induce retinal neovascularization.

Each animal is glucose-tested and photographed with a fundus camera on a weekly basis to record the progression of diabetic retinopathy. Approximately 20-30 minutes prior to starting pictures, one drop of 1% atropine is placed in each eye. The rats are anesthetized with sodium pentobarbital, at a dose of 60 mg/kg, to keep them immobile, and then injected ip with 0.1 ml of 25% fluorescein, which is used to visualize the retinal blood vessels when illuminated by blue light, and to determine the relative leakage of blood by the intensity in the background. The retinal leakage score is determined by digital analysis of the vascular and extravascular fluorescence.

Rats treated with PTZ show significantly increased retinal leakage scores compared to vehicle-treated controls. Treatment with 1, 5, and 10 µM or other concentrations of Compounds XXII, XXIII, or XXV decrease the retinal leakage score of PTZ-treated rats back to the level of controls.

After 14 days, rats are sacrificed and their retinas examined for retinal mRNA and protein levels of intercellular adhesion molecule (ICAM)-1, vascular endothelial growth factor (VEGF) by RT-PCR and ELISA.

RT-PCR for Intercellular Adhesion Molecule-1 and Vascular Endothelial Growth Factor Receptor-1 and -2

Total RNA is isolated from the retina using extraction reagent (Isogen; Nippon Gene, Toyama, Japan) and reverse-transcribed with a cDNA synthesis kit (First-Strand; Pharmacia Biotech, Uppsala, Sweden) according to the manufacturer's protocols. PCR is performed with Taq DNA polymerase (Toyobo, Tokyo, Japan) in a thermal controller (MiniCycler; MJ Research, Watertown, Mass.). The primer sequences are as follows: 5'-ATG TGG CAC CAC ACC TTC TAC AAT GAG CTG CG-3' (sense) and 5'-CGT CAT ACT CCT GCT TGC TGA TCC ACA TCT GC-3' (antisense; 37 bp) for β-actin, 5'-GTG TCG AGC TTT GGG ATG GTA-3' (sense) and 5'-CTG GGC TTG GAG ACT CAG TG-3' (antisense; 505 bp) for mouse intercellular adhesion molecule (ICAM)-1. Human/mouse vascular endothelial growth factor receptor-1 (VEGF R1) primers (302 bp; PCR Primer Pair; R&D Systems, Inc., Minneapolis, Minn.) and human/mouse VEGF R2 primers (569 bp; PCR Primer Pair; R&D Systems, Inc.) are used for VEGFR-1 and -2, respectively.

ELISA for ICAM-1 and VEGFR-1 and -2

The animals are killed with an overdose of anesthesia, and the eyes are immediately enucleated. The retina is carefully isolated and placed into 200 µL lysis buffer (0.02 M HEPES, 10% glycerol, 10 mM $Na_4P_2O_7$, 100 µM $Na_3VO_4$, 1% Triton, 100 mM NaF, 4 mM EDTA [pH 8.0]) supplemented with protease inhibitors, and sonicated. The lysate is centrifuged at 15,000 rpm for 15 minutes at 4° C., and the ICAM-1 and VEGFR-1 and -2 levels in the supernatant are determined with mouse ICAM-1 and VEGFR-1 and -2 kits (Techne Corp., Minneapolis, Minn.) according to the manufacturer's protocol. The tissue sample concentration is calculated from a standard curve and corrected for protein concentration.

Treatment with 1, 5, and 10 µM and other concentrations of Compounds XXII, XXIII, or XXV dose-dependently decreases the levels of ICAM-1 and VEGF in PTZ-treated rats back to the level of controls.

Example 3

Effect of Lipid Conjugates in Patients with Diabetic Retinopathy

Plasma samples are collected from Type I diabetic patients. Their grade of retinopathy is characterised according to a modified Airlie house technique: (a) no retinopathy (n=6), (b) background retinopathy (n=10), (c) proliferative retinopathy (n=6), and (d) advanced proliferative retinopathy requiring vitrectomy (n=16). Plasma samples from non-diabetic age-matched control subjects are also collected. Vitreous samples are collected from patients with advanced proliferative diabetic retinopathy prior to undergoing vitrectomy. Research Ethics Committee approval and informed consent are obtained from all patients.

Plasma and Vitreous Samples

Venous blood samples are collected from the patients and control subjects. Plasma is harvested by centrifugation, aliquoted and stored at −70° C. Approximately 0.5-1 ml of undiluted vitreous fluid is collected from the eye prior to irrigation of the vitreous, transported on dry ice and stored at −70° C.

Enzyme-Linked Immunosorbent Assay (ELISA) for CD105

White 96-well micro-titre plates are coated with anti-CD105 Mab E9 (100 µl/well) diluted 1/1000 in 0.1 M PBS, and incubated in a humidified chamber overnight at 4° C. The coated plates are blocked using 1% BSA and 0.1% Tween 20 in 0.1 M PBS (PBS-Tween) for 2 h at room temperature. Test samples, 1/2 diluted in PBS-Tween, are added to the plates in duplicate. Plasma with pre-determined CD105 (100 ng/ml) is titrated to make a standard curve in each plate. After overnight incubation at 4° C., biotinylated Mab E9 (1/2000 dilution), 100 µl/well, is added to the plates, followed by incubation at 4° C. in a humidified chamber for 3 h. HRP-conjugated avidin at 1/2000 dilution in PBS-Tween and 1% BSA is added (100 µl/well), and plates are incubated at room temperature for 30 min. Three washes with PBS-Tween are carried out between each of the procedures. Finally, 100 µl/well of Amerlite signal reagent (Amersham UK) are added to each well and light emission is measured immediately at 420 nm in an Amerlite plate reader (Kodak Clinical Diagnostics, Aylesbury, UK).

Indirect Immunoassay for VEGF

White 96-well plates are coated with 100 µl/well of goat anti-VEGF-165 antibody (R&D systems), diluted 1/1000 (1 µg/ml) in 0.1M carbonate buffer (pH 9.6), and incubated in a humid box overnight at 4° C. The coated plate is blocked with 1% (w/v) bovine serum albumin (BSA), 0.01% (v/v) Tween 20 in 0.1 M PBS (PBSTween) for 2 h at room temperature. Serum samples are added in duplicate to the plates (100 µl/well, diluted 1/2 in PBS-Tween). A standard curve is generated using recombinant human VEGF (R & D systems) in a range of 0.1-40 ng/ml on each plate. After overnight incubation at 4° C., rabbit anti-VEGF antibody (Santa Cruz Biotechnology) is added (100 µl/well) to the plate at 1/2000 dilution (1 µg/ml) in PBS-Tween and incubation is carried out for 3 h at 4° C. This is followed by the addition of HRP-conjugated goat anti-rabbit antibody (0.5 µg/ml) (diluted 1/2000 with 1% BSA in PBSTween), and additional incubation with shaking for 30 min at room temperature. Three washes with PBS-Tween are carried out between each of the steps. Finally, 100 µl/well of Amerlite chemiluminescence signal reagent are added and the plate is read immediately in a plate reader. The measured values of light emission are converted into absolute concentration by reference to the VEGF standard curve.

Treatment with 1, 5, and 10 µM and other concentrations of Compounds XXII, XXIII, or XXV dose-dependently decreases the plasma levels of CD105 and vitreous levels of VEGF in patients with diabetic retinopathy. In addition, fluorescein angiography, retinal photography, and ultrasound imaging of the eye are used to evaluate progression of the disease.

Example 4

Effect of Contact Lens Solution Comprising Lipid Conjugates on Protein and Lipid Deposition Contact lenses are exposed to both a protein and lipid artificial deposition solution (ATS) in order to assess both the deposit inhibition of the contact lens solution of the instant invention compared to a solution known in the Art, such as ReNu® Rewetting Drops which contains 0.10% poloxamine, 0.50% boric acid, 0.35% sodium borate, 0.40% sodium chloride, 0.10% EDTA, and 0.15% sorbic acid. To test for deposit inhibition, lenses are preconditioned with the solution of the instant invention by soaking the lens in the solution for one hour prior to deposition. After deposition and incubation, the lenses are rinsed with 0.9% saline solution (without sorbic acid).

A. Protocol for Testing Protein Deposit Inhibition:

For preparation of the standards, unworn contact lenses are taken out of their vials, left to air-dry and then placed in glass test tubes along with standard BSA solution. An in vitro protein mixture consisting of lysozyme, lactoferrin, human serum albumin and mucin in MOPS buffer is used. The pH of the solution is adjusted to 7.2 using 1 N HCl and an osmolality equal to 326 mOsm. After one hour of pre-soaking, the lenses are removed from the formulation and placed in 1.5 ml of the protein mix. The lenses are then incubated in the protein mix at 37° C. in a shaking water bath for 48 hours. Protein analysis is done using the calorimetric BCA analytical method (Sigma). The method employs the protein induced reduction of Cu(II) to Cu(I). A purple complex (Amax=562 nm) is formed following the addition of bicinchoninic acid (BCA) to the reduced copper. The intensity of the complex is directly proportional over the protein concentration range of 5 μg/ml to 2000 μg/ml. Following incubation at 37° C., the rate of color development is slowed sufficiently to allow large numbers of samples to be assayed in a single run. The standard protein solution utilized is BSA with a standard concentration range of 0 to 50 μg. Two mls of a mixture of bicinchoninic acid (BCA) and Cu(II) sulfate is added to each test tube, which are then vortexed. Tubes are then covered and placed in a water bath at 37° C. for 15 minutes. After incubation, the purple complex develops. Samples and standards are read in a spectrophotometer at 562 nm. Protein concentration is determined from a standard plot of absorbency vs. concentration (μg).

B. Protocol for Testing Lipid Deposit Inhibition:

Seven contact lenses per test solution are preconditioned with the respective test formulations by soaking the lenses in the formulation for one hour. The lenses are removed from the formulation, and placed in 1.5 mls of a lipid mix (palmitic acid methyl ester (PAME), cholesterol, squalene and mucin in MOPS buffer). Mucin is utilized as a surfactant to aid in the solubilization of the lipids. Lenses are then incubated in the lipid mix at 37° C. in a shaking water bath for 24 hours. After incubation, the lenses are removed from the test solution and rinsed with physiological saline solution (without sorbic acid) to remove any residual deposition solution. Lenses are then placed in glass vials for extraction. A three-hour 1:1 $CHCl_3$/MeOH extraction is subsequently followed by a three-hour hexane extraction. Extracts are then combined and run on a Hewlett Packard GC. The column utilized is an HP-Ultra 1 with an FID detector and He as the carrier gas. Standard solutions of each of the lipids in the deposition mix are made in 1:1 $CHCl_3$/MeOH and the concentration of lipid extracted from the lenses is determined.

C. Results:

The protein and lipid deposition values for the contact lenses pre-soaked in control solution provide a baseline with which to assess the potential cleaning efficacy and deposit inhibition attributes of each of the formulations tested. The contact lens solution of the instant invention inhibits both lipid and protein deposition, indicating that the test formulations are coating the lens in such a way as to hinder lipid and protein uptake.

Example 5

Safety and Tolerability of Contact Lens Solution Comprising Lipid Conjugates

Twenty (20) subjects are enrolled in a 4-hour non-dispensing study comparing the contact lens solution comprising lipid-conjugates to contact lens solution comprising unconjugated GAGs or to ReNu® Rewetting Drops. The subjects are all habitual soft spherical contact lens wearers. Their mean spherical Rx's are determined for test and control eyes. Each subject wears a pair of contact lenses for approximately 4 hours. The eye receiving the test solution is randomly selected and remains constant for the duration of the study. Subjects are asked to place two drops of each solution into the appropriate eye every hour until the four-hour visit. The subjects and investigator are blinded to solution identity. Prior to lens insertion, a spherical refraction is performed through which high contrast visual acuity with high ambient illumination (HCHI) is measured. Corneal and conjunctival staining and limbal and bulbar injection are assessed with the slitlamp. Each subject is then fitted with a pair of contact lenses of their prescription. Each lens is evaluated for centration and movement, comfort, and deposits/wettability. A spherical over-refraction is then performed. The endpoint of the over-refraction is compared to the refractive endpoint to determine the apparent "on-eye" lens power. LogMAR visual acuity under HCHI testing conditions is measured through the over-refraction. Finally, two drops of each solution are instilled into the appropriate eyes, and the subject is asked to rate any sting/burn and the amount. Testing is repeated at the four-hour visit in reverse order, except without repeating the baseline refraction. A two-way ANOVA incorporating Time and Solution is used to test for differences in each of the parametric dependent variables measured. Non-parametric data are analyzed by Friedman ANOVA. Differences at the $p \leq 0.05$ level are considered to be statistically significant.

Subjects are evaluated for the effects of the solution comprising lipid-conjugates for comfort, apparent lens Rx power, and sting/burn visual analog score (i.e. lower sting/burn), lens movement/centration, and anterior ocular physiology in the eye treated with lipid-conjugate solutions compared to the eye treated with control solution.

Example 6

Safety and Tolerability of Contact Lens Packaging Solution Comprising Lipid Conjugates Materials and Methods Contact lenses were exposed to a solution comprising lipid conjugates in order to assess their efficacy as a comfort ingredient in a contact lens solution. Five lipid conjugate compounds, Cpd LI (AlgPE: 120), Cpd XXV (CSAPE: 120), Cpd XL (HemPE:75), Cpd XXV111 (HesDMPE:90 (HetaStarch)) and Cpd XXVI (CMPE:75), were tested.

Cpd LI, Cpd XXV, Cpd XL, Cpd XXVIII and Cpd XXVI were tested for their solubility in an aqueous solution containing $Na_2HPO_4 \times 7H_2O$, $NaH_2PO_4$ and NaCl, pH 7.3, with an osmolality of 250 mOsm/kg.

PV lenses were tested for lens compatibility and stability. Each lens was soaked in a glass vial containing 3 ml of a solution of one of the following: Cpd XXV, Cpd XL, Cpd XXVIII or Cpd XXVI. The glass vials were autoclaved at 121-123° C. for 30 min. The lenses and the solutions were examined for optical parameters and physical appearance immediately following autoclaving and again after one month at 40° C.

Cytotoxic effects of the compounds XXV, XL, XXVIII and XXVI on kidney (MDCK) and SV40 human corneal (HCEC) epithelial cells were evaluated. Each of the compounds in solution was added to MDCK and HCEC cell culture models, with physiological saline or HBSS serving as a control. The compounds were individually tested for their toxicity to L929 mouse fibroblasts in an agar diffusion model, in which cells were separated from each compound by a layer of agar. In this test only compounds that can diffuse through the agar and are toxic to the cells are detected. The L929 monolayer cultures were incubated with the compounds, and observed for cytotoxicity.

PV lenses were soaked in solutions of the compounds and tested. In vivo evaluation was assessed in a one-day rabbit ocular irritation experiment. PV lenses were soaked in solutions of the compounds and placed on the corneas of test rabbits.

Results

Cpds XXV, XL and XXVIII were soluble. Cpd XXVI was soluble upon autoclaving the solution. Cpd LI was insoluble.

The optical parameters and physical appearance of the contact lenses immediately following autoclaving were within industry specifications. There were no significant changes in the pH or osmolality of any of the solutions. A follow-up check one month later also revealed no significant changes in either lens or solution parameters.

Results with the compounds on MDCK and HCEC paralleled those of the controls. No cytotoxicity to L929 monolayer cultures was noted.

No or low levels of ocular irritation were observed with the PV lenses in vivo. There was no statistical difference between treated vs. control PV lenses.

It will be appreciated by persons skilled in the art that the present invention is not limited by what has been particularly shown and described herein above and that numerous modifications, all of which fall within the scope of the present invention, exist. Rather, the scope of the invention is defined by the claims which follow:

What we claim is:

1. A method of treating a disease or disorder of the eye in a subject comprising the step of contacting said subject with a compound comprising a lipid or phospholipid moiety bound optionally via a spacer to a physiologically acceptable monomer, dimer, oligomer, or polymer via an ester or amide bond, and/or a pharmaceutically acceptable salt or a pharmaceutical product thereof, wherein the compound is represented by the structure of the general formula (A):

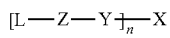
(A)

wherein
L is a lipid or a phospholipid;
Z is either nothing, ethanolamine, serine, inositol, choline, phosphate, or glycerol;
Y is either nothing or a spacer group ranging in length from 2 to 30 atoms;
X is polygeline or polypyranose; and
n is a number from 2 to 1000;
wherein any bond between L, Z, Y and X is either an amide or an esteric bond and the disease or disorder of the eye is retinopathy, glaucoma, macular degeneration or retinal detachment.

2. The method according to claim 1, wherein said retinopathy is diabetic retinopathy, or solar retinopathy.

3. The method according to claim 1, wherein said phospholipid moiety is phosphatidylethanolamine.

4. The method according to claim 3, wherein said phosphatidylethanolamine is dipalmitoyl phosphatidylethanolamine.

5. The method according to claim 3, wherein said phosphatidylethanolamine is dimyristoyl phosphatidylethanolamine.

6. The method according to claim 1, wherein said polypyranose is carboxymethylcellulose.

7. The method according to claim 1, wherein said polypyranose is alginate.

8. The method according to claim 1, wherein said polypyranose is hydroxyethyl starch.

9. The method of claim 1, wherein L is phosphatidyl, Z is ethanolamine, Y is nothing, and X is carboxymethylcellulose or a glycosaminoglycan.

10. The method of claim 1, wherein the phosphatidylethanolamine moiety is dipalmitoyl or dimyristoyl phosphatidylethanolamine.

11. The method according to claim 1, wherein the phospholipid is phosphatidic acid, monoacylglycerol, diacylglycerol, triacylglycerol, sphingosine, sphingomyelin, chondroitin-4-sulfate, chondroitin-6-sulfate, ceramide, phosphatidylethanolamine, phosphatidylserine, phosphatidylcholine, phosphatidylinositol, or phosphatidylglycerol.

12. The method according to claim 1, wherein said compound is represented by the structure of the general formula (I):

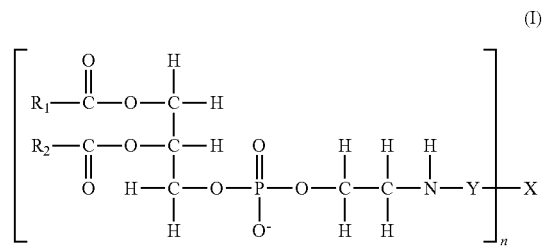
(I)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms; and
Y is either nothing or a spacer group ranging in length from 2 to 30 atoms;
X is polygeline; and
n is a number from 2 to 1000.

13. The method according to claim 1, wherein said compound is represented by the structure of the general formula (I):

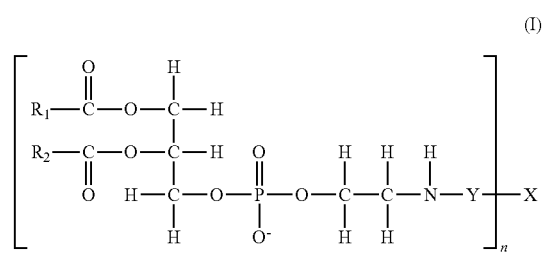
(I)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms; and
Y is either nothing or a spacer group ranging in length from 2 to 30 atoms;
X is a polypyranose; and
n is a number from 2 to 1000.

14. The method according to claim 13, wherein the polypyranose is carboxymethylcellulose.

15. The method according to claim 13, wherein the polypyranose is alginate.

16. The method according to claim 13, wherein the polypyranose is hydroxyethyl starch.

17. The method according to claim 12, wherein n is a number from 2 to 200.

18. The method according to claim 13, wherein n is a number from 2 to 200.

19. A method of treating a disease or disorder of the eye in a subject comprising the step of contacting said subject with a compound and/or a pharmaceutically acceptable salt or a pharmaceutical product thereof, wherein said compound is represented by the structure of the general formula (I):

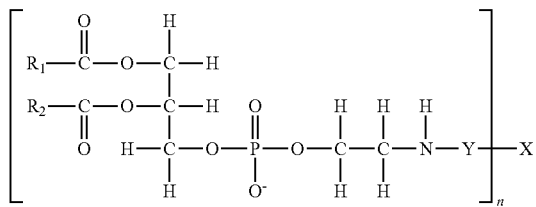

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms; and Y is either nothing or a spacer group ranging in length from 2 to 30 atoms;

X is a glycosaminoglycan; and n is a number from 2 to 1000;

wherein if Y is nothing the phosphatidylethanolamine is directly linked to X via an amide bond and if Y is a spacer, said spacer is directly linked to X via an amide or an esteric bond and to said phosphatidylethanolamine via an amide bond; and wherein said disease or disorder of the eye is retinopathy, glaucoma, macular degeneration or retinal detachment.

20. The method of claim 19, wherein n is a number from 2 to 100.

21. The method of claim 19, wherein X is hyaluronic acid, heparin or chondroitin sulfate.

22. The method according to claim 19, wherein X is hyaluronic acid, and $R_1$, and/or $R_2$ is a palmitic acid moiety.

23. The method according to claim 19, wherein X is hyaluronic acid, and $R_1$, and/or $R_2$ is a myristic acid moiety.

24. The method according to claim 19, wherein X is heparin, and $R_1$, and/or $R_2$ is a palmitic acid moiety.

25. The method according to claim 19, wherein X is heparin, and $R_1$, and/or $R_2$ is a myristic acid moiety.

26. The method according to claim 19, wherein X chondroitin sulfate, and $R_1$, and/or $R_2$ is a palmitic acid moiety.

27. The method according to claim 19, wherein X is chondroitin sulfate, and $R_1$, and/or $R_2$ is a myristic acid moiety.

* * * * *